(12) United States Patent
Orchard et al.

(10) Patent No.: US 7,105,554 B2
(45) Date of Patent: Sep. 12, 2006

(54) BENZYLIDENE THIAZOLIDINEDIONES AND THEIR USE AS ANTIMYCOTIC AGENTS

(75) Inventors: Michael Glen Orchard, Oxfordshire (GB); Judi Charlotte Neuss, Oxfordshire (GB); Carl Maurice Swedler Galley, Avon (GB)

(73) Assignee: Oxford Glycosciences (UK) Ltd., Abingdon (GB)

( * ) Notice: Subject to any disclaimer, the term of this patent is extended or adjusted under 35 U.S.C. 154(b) by 305 days.

(21) Appl. No.: 10/371,964

(22) Filed: Feb. 21, 2003

(65) Prior Publication Data

US 2004/0006112 A1 Jan. 8, 2004

Related U.S. Application Data

(63) Continuation of application No. PCT/GB01/03862, filed on Aug. 30, 2001.

(30) Foreign Application Priority Data

Aug. 31, 2000 (GB) ................................. 0021421.3

(51) Int. Cl.
*A61K 31/426* (2006.01)
*C07D 277/26* (2006.01)

(52) U.S. Cl. ..................................... 514/369; 548/183

(58) Field of Classification Search ................ 548/183; 514/369

See application file for complete search history.

(56) References Cited

U.S. PATENT DOCUMENTS 5,716,975 A * 2/1998 Bue-Valleskey et al. .... 514/369

FOREIGN PATENT DOCUMENTS

| WO | WO 94/29287 | 12/1994 |
|----|-------------|---------|
| WO | WO 00/18746 | 4/2000 |
| WO | WO 00/18747 | 4/2000 |
| WO | WO 01/57006 | 8/2001 |

OTHER PUBLICATIONS

Wang Chunde et al., CA 121:108599, 1994.*
AN 1968-49496, Chem Abs. Service, XP002183084, 1968.
AN 1970-121421, Chem Abs. Service, XP002183085, 1970.
AN 1973-71975, Chem Abs. Service, XP002183087, 1973.
AN 1973-492084, Chem Abs., XP002183088, 1973.
AN 1986-442785, Chem Abs Service, XP002183081 (JP 61056175), Mar. 20, 1986.
AN 1995-71953, Chem Abs. Service, XP002183086, 1995.
AN 1996-440644, Chem Abs. Service, XP002183083 (JP 8109174), Apr. 30, 1996.
AN 1996-440646, Chem Abs Service, XP002183082, (JP 8109175), Apr. 30, 1996.
AN 1997-010295, Derwent Publications Ltd., XP002183089 and SU 1417436A, Apr. 27, 1996.
Search Report mailed Dec. 3, 2001 in International Appliction No. PCT/GB01/03862.

* cited by examiner

*Primary Examiner*—Laura L. Stockton
(74) *Attorney, Agent, or Firm*—Darby & Darby

(57) ABSTRACT

A compound of formula I or a salt thereof wherein, A is O or S, X and Y independently represent O, $CH_2$ and may be the same or different, Q is $(CH_2)_m$—$CH(R1)$-$(CH_2)_n$, R is OR6, NHR8, R1 is hydrogen, or optionally substituted alkyl, R2 and R3 are independently hydrogen, or specific substituents, provided that R2 and R3 are not both H, and R4 and R5 are hydrogen or specific substituents, m is 0–3; n is 0–2; are useful in the treatment of fungal infections.

16 Claims, No Drawings

BENZYLIDENE THIAZOLIDINEDIONES AND THEIR USE AS ANTIMYCOTIC AGENTS

CROSS REFERENCE TO RELATED APPLICATIONS

This is a Continuation of International Application No. PCT/GB01/03862 filed Aug. 30, 2001, which claims priority of United Kingdom Application No. 0021421.3, filed Aug. 31, 2000. The International Application was published in English on Mar. 7, 2002 as WO 02/17915 A1 under PCT Article 21(2).

The present invention relates to the use of a compound of the invention in the preparation of a medicament for use as an antifungal agent. The invention also relates to methods of treating an individual susceptible to or suffering from an antifungal infection. In addition, the invention relates to novel compounds, their synthesis, pharmaceutical compositions comprising the novel compounds and the first medical uses of the novel compounds.

Fungal infections can affect animals including humans. These can include infections of the joints and skin. Some fungal infections occur as a result of opportunistic infection of a weakened or immune-suppressed individual. The incidence of life-threatening fungal infections has increased dramatically as the population of immunocompromised individuals (including cancer, organ transplant and AIDS patients) has increased. Present therapeutic options for the treatment of these infections are limited to two classes of compound: polyenes and azoles. The utility of polyenes is limited by nephrotoxicity and resistance is emerging to azoles. There is therefore a need for new anti-fungal compounds with novel mechanisms of action for use in treating or preventing such fungal infections.

WO94/29287 discloses arylidene-4-oxo-2-thioxo-3-thiazolidine carboxylic acids of the formula

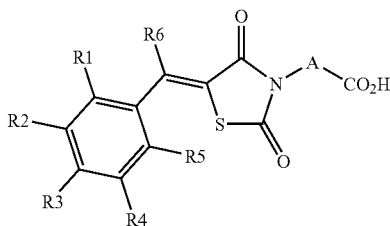

and their use in the treatment of atherosclerosis, arteriosclerosis and the late effects of diabetes.

WO00/18747 discloses rhodanine carboxylic acid derivatives of the formula

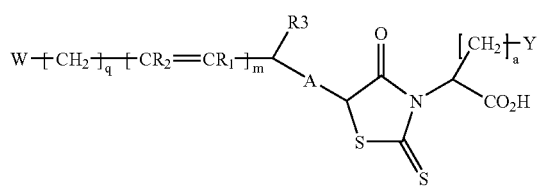

for the treatment and prevention of metabolic bone disorders.

We have now found that certain thiazolidine derivatives exhibit antifungal activity.

The first aspect of the present invention relates to the use of a compound of formula I or a salt thereof

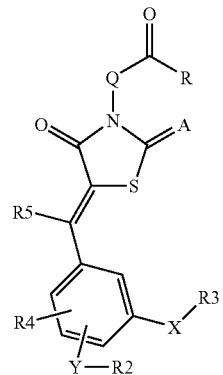

Formula I in the manufacture of a medicament for use as an antifungal agent wherein, A is O or S, X and Y independently represent O, $CH_2$ and may be the same or different, Q is $(CH_2)_m$—$CH(R1)$-$(CH_2)_n$, R is OR6, NHR8, R1 is hydrogen, $C_1$–$C_6$ branched or straight chain alkyl optionally substituted with one or more of hydroxyl, COR, $C_1$–$C_3$ alkylphenyl or phenyl, R2 and R3 are independently hydrogen, $C_1$–$C_{10}$ branched or straight chain alkyl optionally substituted by $C_3$–$C_6$ cycloalkyl, $C_1$–$C_6$ cycloalkyl, $C_1$–$C_{10}$ branched or straight chain alkenyl, $C_1$–$C_{10}$ branched or straight chain alkynyl, $(CH_2)_m$—$(CF_2)_n$$CF3$ or $(CH_2)_n$—$CH(R11)$-$(CH_2)_q$-aryl where aryl is phenyl, pyridyl, thienyl, or furyl wherein phenyl is optionally substituted by one or more substituents selected from F, Cl, Br, $CF_3$, $OCF_3$, OR7, $C_1$–$C_6$ branched or straight chain alkyl, COR, CN, $SO_2R9$, SONR8R9, and pyridyl, thienyl or furyl are optionally substituted by F, Cl, Br, $CF_3$, OR6, $C_1$–$C_6$ branched or straight chain alkyl, provided that R2 and R3 are not both H, with the option that when X is $CH_2$ then R3 may be OR6 and when Y is $CH_2$, then R2 may be OR6;

R2 and R3 may together form the group $(CH_2)_q$CHR10,

R4 is hydrogen, F, Cl, Br, $CF_3$, OR6, $C_1$–$C_6$ branched or straight chain alkyl or $O(CH_2)_n$—$CH(R11)$-$(CH_2)_q$-aryl where aryl is phenyl, pyridyl, thienyl, or furyl wherein phenyl is optionally substituted by one or more substituents selected from F, Cl, Br, $CF_3$, $OCF_3$, OR6, $C_1$–$C_6$ branched or straight chain alkyl, COR, CN, $SO_2R9$, SONR8R9, and pyridyl, thienyl or furyl are optionally substituted by F, Cl, Br, $CF_3$, OR6, $C_1$–$C_6$ branched or straight chain alkyl, R5 is hydrogen, $C_1$–$C_6$ branched or straight chain alkyl, phenyl optionally substituted by one or more substituents selected from F, Cl, Br, $CF_3$, $OCF_3$, OR6, $C_1$–$C_6$ branched or straight chain alkyl, COR, CN, $SO_2R9$, R6 and R7 are independently hydrogen, $C_1$–$C_6$ branched or straight chain alkyl or cycloalkyl, or aryl, wherein aryl is phenyl optionally substituted by one or more substituents selected from F, Cl, Br, $CF_3$, $OCF_3$, $C_1$–$C_6$ branched or straight chain alkyl, COR, CN, SOR8, R8 is hydrogen, $C_1$–$C_3$ alkyl, R9 is $C_1$–$C_6$ branched or straight chain alkyl or cycloalkyl, phenyl, $C_1$–$C_3$ alkylphenyl R10 is hydrogen, $C_1$–$C_{10}$ branched or straight chain alkyl, $(CH_2)_p$-Aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$, R11 is hydrogen, $C_1$–$C_6$ branched or straight chain alkyl, $CF_3$, $CO_2H$, $CO_2R6$, $CONR6R9$, $C_1$–$C_6$ branched or straight chain alkyl substituted by hydroxyl, $CO_2H$, $CO_2R6$ or $CONR6R9$;

taken together R6 and R9 may form a ring e.g. a piperidine ring, optionally incorporating one or more additional heteroatoms (e.g. a piperazine ring); wherein the ring may be optionally substituted by one or more of branched or unbranched $C_1$–$C_6$ alkyl, aryl, alkylaryl wherein aryl is preferably phenyl.

m is 0–3; n is 0–2; p is 0–4; q is 0–1

In a preferred embodiment the use of compounds of formula I in which:

A is O or S;

X and Y are independently O or $CH_2$;

Q is CH(R1);

R is OR6 or $NH_2$;

R1 is hydrogen, $C_1$–$C_6$ branched or straight chain alkyl optionally substituted with one or more phenyl groups;

R2 and R3 are independently pyridyl, $C_1$–$C_{10}$ branched or straight chain alkyl, optionally substituted with cyclhexyl, $(CH_2)_n(CF_2)_mCF_3$, CH(R11)-phenyl or $CH_2CH(R11)$-phenyl, where phenyl is optionally substituted by one or more substituents selected from F, Cl, $CF_3$, $C_1$–$C_6$ branched or straight chain alkyl, OR7 or $SO_2R9$;

R4 is hydrogen or O—$CH_2$-phenyl;

R5 is hydrogen or $C_1$–$C_6$ branched or straight chain alkyl;

R6 is hydrogen or $C_1$–$C_6$ branched or straight chain alkyl;

R7 is $C_1$–$C_6$ branched or straight chain alkyl;

R9 is $C_1$–$C_6$ branched or straight chain alkyl or cycloalkyl, phenyl or $C_1$–$C_3$ alkylphenyl;

R11 is $CO_2R6$, $CONR6R9$, $C_1$–$C_6$ branched or straight chain alkyl optionally substituted by hydroxy or R6 and R9 may together form a ring e.g. a piperidine ring, optionally incorporating one or more additional heteroatoms (e.g. a piperazine ring), where the ring may be optionally substituted by one or more of $C_1$–$C_6$ branched or straight chain alkyl or phenyl is provided.

Examples of pharmaceutically acceptable salts of the above compounds include those derived from inorganic and organic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases that are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like. Where appropriate salts can also be formed with organic acids such as methanesulphonic acid, benzenesulphonic acid and p-toluenesulphonic acid, or mineral acids such as hydrochloric and sulphuric acid and the like, giving methanesulphonate, benzenesulphonate, p-toluenesulphonate, hydrochloride and sulphate salts, and the like, respectively.

Salts may be prepared in a conventional manner using methods well known in the art.

The invention also extends to prodrugs of the aforementioned compounds. A prodrug is commonly described as an inactive or protected derivative of an active ingredient or a drug which is converted to the active ingredient or drug in the body. In addition, the invention extends to active derivatives of the aforementioned compounds.

Where a compound of the invention contains one or more chiral centres, the compound can be provided as a single isomer (R or S) or a mixture of isomers for example, a racemic mixture. Where a compound contains an alkene moiety, the alkene can be presented as a cis or trans isomer or a mixture thereof.

The medicament of the first aspect of the invention is provided as an antifungal agent. For the purposes of this invention, the medicament can be used in the curative or prophylatic treatment of fungal infections in humans and animals.

For the purposes of this invention, an anti-fungal agent is a compound or composition which alleviates or reduces the symptoms of a fungal infection or an agent which causes harm to fungus allowing the destruction of a fungus either by the agent, a second agent or the hosts natural defenses (e.g. the immune system).

This aspect provides a medicament which can be administered to humans or animals especially domestic animals such as dogs, cats, horses etc.

The medicament comprising one or more compound of formula I will usually be supplied as part of a sterile, pharmaceutical composition which will normally include a pharmaceutically acceptable carrier. This pharmaceutical composition may be in any suitable form, depending on the desired method of administering it to a patient.

It may be provided in unit dosage form, will generally be provided in a sealed container and may be provided as part of a kit. Such a kit would normally (although not necessarily) include instructions for use. It may include a plurality of said unit dosage forms.

The medicament of the first aspect of the invention is particularly useful in treating topical infections caused by species of fungus including *Candida, Trichophyton, Microsporum* and *Epidermophyton* or in mucosal infections caused by species of fungus including *Candida albicans* (e.g. thrush and vaginal candidiasis). They can also be used in the treatment of infections caused by, for example, species of *Candida* (e.g. *Candida albicans*), *Cryptococcus neoformans, Aspergillus flavus, Aspergillus fumigatus, Coccidioides, Paracoccidioides, Histoplasma* or *Blastomyces*.

The cell wall of *Candida* and other pathogenic fungal species is essential for the survival of the organism. Defects in the wall structure will result in cell swelling and ultimately death through rupture. The unique nature of the wall has made its synthesis and re-modelling a focus for the development of novel anti-fungal agents. The wall consists of three major components: complex β1-3 and β1-6 linked glucan chains, chitin and cell wall mannoproteins. The β-glucans represent 50–60% of the cell wall mass, forming a rigid skeletal structure responsible for shape and physical strength. The chitin is only a minor component (>3%), but forms a structure to which the β-glucan is linked and is essential for bud scar formation during cell division. There are a number of agents that are being developed as anti-fungal treatments targeted against β-glucan (lipopeptides, e.g. echinocandins and pneumocandins (Kurtz, M. B. & Douglas, C. M. (1997) J. Med. Vet. Myc. 35, 79–86.)) and chitin (e.g. nikkomycin Z (Obi, K. Uda, J. Iwase, K. Sugimoto, O. Ebisu, H. & Matsuda, A. (2000) Bioorg. Med. Chem. Lett. 10, 1451–4)) synthesis.

The mannoproteins represent the remaining content of the wall. They form radially extending fibrillae at the outside of the cell wall and are believed to confer the cell surface properties involved in adhesion and host interactions. A number of classes of mannoproteins have been identified (e.g. Sed1, Flo11, Aga1, Pir2, Als1, Axl2) and these have been separated into groups dependent upon the nature of their attachment to the other cell wall components (Kapteyn, J. C. Hoyer, L. L. Hecht, J. E. Muller, W. H. Andel, A. Verkleij, A. J. Makarow, M. Van Den Ende, H. & Klis, F. M. (2000) Mol. Microbiol. 35, 601–11). During their secretion from the cell some receive a GPI anchor and all become mannosylated. Mannosylation of these proteins is divided into two categories: O- and N-linked. The N-linked are attached via asparagine residues and form extensive branched structures consisting of an α1,6 backbone to which α1,2-, α1,3- and β1,2-side chains are attached. The O-linked are attached via serine or threonine residues and consist of short linear chains. The extension of both chain types is catalysed by a family of mannosyltransferases. The initial mannose residue is added to serine or threonine by a protein:mannosyl transferase (PMT) which uses dolichol-phospho-mannose as a donor of the mannose. Seven PMT's have been reported in *S. cerevisiae* (Strahl-Bolsinger, S. Gentzsch, M. & Tanner, W. (1999) Biochim. Biophys. Acta. 1426, 297–307) and by homology five have been identified to date in *Candida* (homologues have also been found in *Aspergillus* and other fungal species). It appears that members of the family show some substrate specificity (Sanders, S. L. Gentzsch, M. Tanner, W. & Herskowitz, I. (1999) J. Cell. Biol. 145, 1177–88) but this has not been clearly defined.

Although a human homologue has been found and evidence of O-mannosylation in some tissues, no activity has been recorded in mammalian tissue.

Deletion of both copies of the PMT1 gene from *Candida albicans* results in a strain that is no longer virulent in animal models (Timpel, C. Strahl-Bolsinger, S. Ziegelbauer, K. & Ernst, J. F. (1998) J. Biol. Chem. 273, 20837–46). The strain also shows a failure to form pseudohyphae under conditions of nitrogen starvation and increased sensitivity to agents associated with cell wall defects.

Without being bound by scientific theory it is proposed that the compounds of the invention inhibit the protein mannosyl transferase enzyme, preventing the formation of the O-linked mannoproteins and compromising the integrity of the fungal cell wall. Defects in the wall structure have been shown to result in cell swelling and ultimately death through rupture.

A second aspect of the invention provides a method of treatment for treating an individual suffering from a fungal infection comprising administering to the individual a compound as defined in the first aspect of the invention. The treatment may be prophylactic or in respect of an existing condition.

The compounds defined in the first aspect can be administered as a pharmaceutical composition in combination with a pharmaceutically acceptable excipient. The pharmaceutical composition can comprise one or more of the compounds of the first aspect. The compound or pharmaceutical composition can be administered simultaneously, separately or sequentially with another anti-fungal treatment.

The method of treatment will provide a compound as defined in the first aspect at an effective dosage of 0.1–750 milligrams/kg/day, preferably 0.1–10 milligrams/kg/day. The compounds can be administered once or more a day, twice a week, weekly, every two weeks or monthly.

A particular feature of the second aspect is the treatment of individuals who are immunosuppressed as a result of a therapy (e.g. chemotherapy or radiotherapy), organ transplant or an infection (e.g. HIV).

The method can be used to treat topical infections caused by species of fungus including *Candida, Trichophyton, Microsporum* and *Epidermophyton* or in mucosal infections caused by species of fungus including *Candida albicans* (e.g. thrush and vaginal candidiasis). The method can also be used in the treatment of infections caused by, for example, species of *Candida* (e.g. *Candida albicans*), *Cryptococcus neoformans, Aspergillus flavus, Aspergillus fumigatus, Coccidioides, Paracoccidioides, Histoplasma* or *Blastomyces*. The compounds of this invention may be used in combination with one or more other antifungal agents.

All preferred features of the first aspect also apply to the second aspect.

The third aspect of the invention provides a novel compound of formula Ia, or salts thereof,

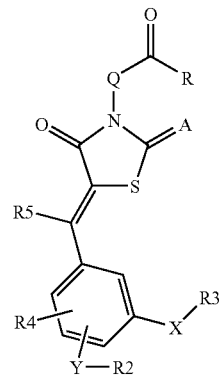

Formula Ia wherein
A is O or S,
X and Y independently represent O, $CH_2$ and may be the same or different,
Q is $(CH_2)_m$—$CH(R1)$-$(CH_2)_n$,
R is OR6, NHR8,
R1 is hydrogen, $C_1$–$C_6$ branched or straight chain alkyl optionally substituted with one or more of hydroxyl, COR, $C_1$–$C_3$ alkylphenyl or phenyl,
R2 and R3 are independently hydrogen, $C_1$–$C_{10}$ branched or straight chain alkyl optionally substituted by $C_3$–$C_6$ cycloalkyl, $C_1$–$C_6$ cycloalkyl, $C_1$–$C_{10}$ branched or straight chain alkenyl, $C_1$–$C_{10}$ branched or straight chain alkynyl, $(CH_2)_m$—$(CF_2)_n CF3$ or $(CH_2)_n$—$CH(R11)$-$(CH_2)_q$-aryl where aryl is phenyl, pyridyl, thienyl, or furyl wherein phenyl is optionally substituted by one or more substituents selected from F, Cl, Br, $CF_3$, $OCF_3$, OR7, $C_1$–$C_6$ branched or straight chain alkyl, COR, CN, $SO_2R9$, SONR8R9, and pyridyl, thienyl or furyl are optionally substituted by F, Cl, Br, $CF_3$, OR6, $C_1$–$C_6$ branched or straight chain alkyl, provided that R2 and R3 are not both H, with the option that when X is $CH_2$ then R3 may be OR6 and when Y is $CH_2$, then R2 may be OR6;
R2 and R3 may together form the group $(CH_2)_q CHR10$, R4 is hydrogen, F, Cl, Br, $CF_3$, OR6, $C_1$–$C_6$ branched or straight chain alkyl or $O(CH_2)_n$—$CH(R11)$-$(CH_2)_q$-aryl where aryl is phenyl, pyridyl, thienyl, or furyl wherein phenyl is optionally substituted by one or more substituents selected from F, Cl, Br, $CF_3$, $OCF_3$, OR6, $C_1$–$C_6$ branched or straight chain alkyl, COR, CN, $SO_2R9$, SONR8R9, and pyridyl, thienyl or furyl are optionally substituted by F, Cl, Br, $CF_3$, OR6, $C_1$–$C_6$ branched or straight chain alkyl, R5 is hydrogen, $C_1$–$C_6$ branched or straight chain alkyl, phenyl optionally substituted by one or more substituents selected from F, Cl, Br, $CF_3$, $OCF_3$, OR6, $C_1$–$C_6$ branched or straight chain alkyl, COR, CN, $SO_2R9$, R6 and R7 are independently hydrogen, $C_1$–$C_6$ branched or straight chain alkyl or cycloalkyl, or aryl, wherein aryl is phenyl optionally substituted by one or more substituents selected from F, Cl, Br, $CF_3$, $OCF_3$, $C_1$–$C_6$ branched or straight chain alkyl, COR, CN, SOR8, R8 is hydrogen, $C_1$–$C_3$ alkyl, R9 is $C_1$–$C_6$ branched or straight chain alkyl or cycloalkyl, phenyl, $C_1$–$C_3$ alkylphenyl R10 is hydrogen, $C_1$–$C_{10}$ branched or straight chain alkyl, $(CH_2)_p$—Aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$, R11 is hydrogen, $C_1$–$C_6$ branched or straight chain alkyl, $CF_3$, $CO_2H$, $CO_2R6$, CONR6R9, $C_1$–$C_6$ branched or straight chain alkyl substituted by hydroxyl, $CO_2H$, $CO_2R6$ or CONR6R9;

taken together R6 and R9 may form a ring e.g. a piperidine ring, optionally incorporating one or more additional heteroatoms (e.g. a piperazine ring); wherein the ring may be optionally substituted by one or more of branched or unbranched $C_1$–$C_6$ alkyl, aryl, alkylaryl wherein aryl is preferably phenyl.

m is 0–3; n is 0–2; p is 0–4; q is 0–1;

with the proviso that when X and Y are both O, R is OH and R4 is hydrogen, $C_1$–$C_6$ alkyl, $C_1$–$C_6$ alkoxy, O—$CH_2$-phenyl or O—$CH_2$-phenyl substituted with $C_1$–$C_4$ alkyl, $C_1$–$C_4$ alkoxy or hydroxy, then R2 and R3 are not hydrogen, $C_1$–$C_6$ alkyl, hydroxy, $CH_2$-phenyl or $CH_2$-phenyl wherein the phenyl is substituted by $C_1$–$C_4$ alkyl, $C_1$–$C_4$ alkoxy or hydroxy.

Preferred compounds of the third aspect of the invention include:

5-[[3,4-Bis[(4-fluorophenyl)methoxy]phenyl]methylene]-4-oxo-2-thioxo-3-thiazolidineacetic acid 5-[[3,4-Bis[(2,4-difluorophenyl)methoxy]phenyl]methylene]-4-oxo-2-thioxo-3-thiazolidineacetic acid 5-[[3-(Phenylmethoxy)-4-[(2-phenyl)ethoxy]phenyl]methylene]-4-oxo-2-thioxo-3-thiazolidineacetic acid 5-[[4-[(3,4-Difluorophenyl)methoxy]-3-(Phenylmethoxy)phenyl]-methylene]-4-oxo-2-thioxo-3-thiazolidineacetic acid 5-[[4-[(4-Trifluoromethylphenyl)methoxy]-3-(phenylmethoxy)-phenyl]methylene]-4-oxo-2-thioxo-3-thiazolidineacetic acid 5-[[3-(Phenylmethoxy)-4-[(3-trifluoromethylphenyl)methoxy]phenyl]-methylene]-4-oxo-2-thioxo-3-thiazolidineacetic acid 5-[[4-[(2,4-Difluorophenyl)methoxy]-3-(phenylmethoxy)phenyl]-methylene]-4-oxo-2-thioxo-3-thiazolidineacetic acid 5-[[3-(Phenylmethoxy)-4-[(4-trifluoromethoxyphenyl)methoxy]-phenyl]-methylene]-4-oxo-2-thioxo-3-thiazolidineacetic acid 5-[[4-[(4-Chlorophenyl)methoxy]3-(phenylmethoxy)phenyl]-methylene]-4-oxo-2-thioxo-3-thiazolidineacetic acid 5-[[4-[[3,5-Bis(trifluoromethyl)phenyl]methoxy]-3-(Phenylmethoxy)-phenyl]-methylene]-4-oxo-2-thioxo-3-thiazolidineacetic acid 5-[[3-[(3,4-Difluorophenyl)methoxy]-4-(phenylmethoxy)phenyl]-methylene]-4-oxo-2-thioxo-3-thiazolidineacetic acid 5-[[4-(Phenylmethoxy)-3-[(alpha-di-n-propylaminocarbonyl)phenyl-methoxy]phenyl]-methylene]-4-oxo-2-thioxo-3-thiazolidineacetic acid 5-[[4-(Phenylmethoxy)-3-[(alpha-2-(phenylethyl)aminocarbonyl)phenylmethoxy-phenyl]methylene]-4-oxo-2-thioxo-3-thiazolidineacetic acid 5-[[4-Phenylmethoxy-3-[(phenoxy)methyl]phenyl]methylene]-4-oxo-2-thioxo-3-thiazolidineacetic acid 5-[[4-(Phenylmethoxy)-3-[(α-(N-benzylaminocarbonyl)phenylmethoxy]phenyl]-methylene]-4-oxo-2-thioxo-3-thiazolidineacetic acid 5-[[4-(Phenylmethoxy)-3-[(α-N-phenylaminocarbonyl)phenylmethoxy]phenyl]-methylene]-4-oxo-2-thioxo-3-thiazolidineacetic acid 5-[[4-(Phenylmethoxy)-3-[(α-2-ethylpiperidinyl-N-carbonyl)phenylmethoxy]phenyl]-methylene]-4-oxo-2-thioxo-3-thiazolidineacetic acid 5-[[4-(Phenylmethoxy)-3-[(α-N-propylaminocarbonyl)phenylmethoxy]-phenyl]methylene]-4-oxo-2-thioxo-3-thiazolidineacetic acid 5-[[4-(Phenylmethoxy)-3-[(α-cis-2,6-dimethylmorpholinyl-N-carbonyl)-phenylmethoxy]phenyl]methylene]-4-oxo-2-thioxo-3-thiazolidineacetic acid 5-[[4-(Phenylmethoxy)-3-[(α-N,N-di-n-butylaminocarbonyl)phenylmethoxy]phenyl]-methylene]-4-oxo-2-thioxo-3-thiazolidineacetic acid 5-[[4-(Phenylmethoxy)-3-[(α-N-n-propyl-N-sec-butylaminocarbonyl)phenylmethoxy]phenyl]methylene]-4-oxo-2-thioxo-3-thiazolidineacetic acid 5-[[4-(Phenylmethoxy)-3-[(α-di-n-propylaminocarbonyl)phenylmethoxy]-phenyl]methylene]-2,4-dioxo-3-thiazolidineacetic acid 5-[[4-(2-Phenylethoxy)-3-[α-di-n-propylaminocarbonyl)phenylmethoxy]phenyl]-methylene]-4-oxo-2-thioxo-3-thiazolidineacetic acid 5-[[4-(2-Phenylethoxy)-3-[(α-2-ethyl-piperidinyl-N-carbonyl)phenylmethoxy]phenyl]-methylene]-4-oxo-2-thioxo-3-thiazolidineacetic acid 5-[[4-(2-Phenylethoxy)-3-[α-N-ethyl-N-cyclohexylaminocarbonyl)phenylmethoxy]phenyl]methylene]-4-oxo-2-thioxo-3-thiazolidineacetic acid 5-[[4-(2-Phenylethoxy)-3-[(α-(4-phenylpiperazinyl)-N-carbonyl)phenylmethoxy]-phenyl]methylene]-4-oxo-2-thioxo-3-thiazolidineacetic acid 5-[[4-(2-Phenylethoxy)-3-[(α-N-ethyl-N-iso-propylaminocarbonyl)-phenylmethoxy]phenyl]methylene]-4-oxo-2-thioxo-3-thiazolidineacetic acid 5-[[4-(2-Phenylethoxy)-3-[(α-N-ethyl-N-cyclohexylaminocarbonyl)phenylmethoxy]phenyl]-methylene]-2,4-dioxo-3-thiazolidineacetic acid 5-[[3-(Phenylmethoxy)-4-[2-(4-chlorophenyl)ethoxy]phenyl]-methylene]-4-oxo-2-thioxo-3-thiazolidineacetic acid 5-[[3-(Phenylmethoxy)-4-[2-(4-fluorophenyl)ethoxy]phenyl]methylene]-4-oxo-2-thioxo-3-thiazolidineacetic acid 5-[[3-(Phenylmethoxy)-4-[(S)-2-phenylpropyloxy]phenyl] methylene]-4-oxo-2-thioxo-3-thiazolidineacetic acid 5-[[3-(Phenylmethoxy)-4-[2-cyclohexylethoxy]phenyl]methylene]-4-oxo-2-thioxo-3-thiazolidineacetic acid 5-[[3-(2-Pyridylmethoxy)-4-(2-phenylethoxy)phenyl]methylene]-4-oxo-2-thioxo-3-thiazolidineacetic acid hydrochloride salt
5-[[3-(1-Phenyl-2,2,2-trifluoroethoxy)-4-[2-phenylethoxy]phenyl]methylene]-4-oxo-2-thioxo-3-thiazolidineacetic acid
5-[[3-[(R)-1-Phenyl-2,2,2-trifluoroethoxy]-4-[2-phenylethoxy]phenyl]methylene]-4-oxo-2-thioxo-3-thiazolidineacetic acid
5-[[3-[(S)-1-Phenyl-2,2,2-trifluoroethoxy]-4-[2-phenylethoxy]phenyl]methylene]-4-oxo-2-thioxo-3-thiazolidineacetic acid
5-[[3-[(S)-1-Phenyl-2,2,2-trifluoroethoxy]-4-[(R)-2-phenylpropoxy]phenyl]-methylene]-4-oxo-2-thioxo-3-thiazolidineacetic acid
5-[[3-[(S)-1-Phenyl-2,2,2-trifluoroethoxy]-4-[(S)-2-phenylpropoxy]-phenyl]methylene]-4-oxo-2-thioxo-3-thiazolidineacetic acid
5-[[3-(Phenylmethoxy)-4-(2,2,3,3,3-pentafluoropropoxy)phenyl]methylene]-4-oxo-2-thioxo-3-thiazolidineacetic acid
5-[[3-(1-Phenylethoxy)-4-(2-phenylethoxy)]phenyl]methylene]-4-oxo-2-thioxo-3-thiazolidineacetic acid
5-[[3-(1-Phenyl-2-hydroxy)ethoxy)-4-(2-phenylethoxy)]phenyl]methylene]-4-oxo-2-thioxo-3-thiazolidineacetic acid
5-[[4-(2-Phenylethoxy)-3-(phenyloxymethyl)]phenyl]methylene]-4-oxo-2-thioxo-3-thiazolidineacetic acid
5-[[3-(Phenylmethoxy)-4-(2-phenylethoxy)phenyl]methylene]-4-oxo-2-thioxo-3-thiazolidineacetamide
Ethyl 5-[[3-(phenylmethoxy)-4-(2-phenethoxy)phenyl]methylene]-4-oxo-2-thioxo-3-thiazolidineacetate The third aspect of the invention also provides novel intermediate compounds in the formation of compounds of formula I.

All preferred features of the first and second aspects of the invention also apply to the third aspect.

The fourth aspect of the invention relates to the following specific compounds which are believed to be novel;
5-[[3-(Phenylmethoxy)-4-[(4-methylphenyl)methoxy]phenyl]-methylene]-4-oxo-2-thioxo-3-thiazolidineacetic acid
5-[[3,4,5-Tris(phenylmethoxy)phenyl]methylene]-4-oxo-2-thioxo-3-thiazolidineacetic acid
5-[[3,4-Bis[(4-methoxyphenyl)methoxy]phenyl]methylene]-4-oxo-2-thioxo-3-thiazolidineacetic acid
5-[[4-Pentyloxy-3-(phenylmethoxy)phenyl]methylene]-4-oxo-2-thioxo-3-thiazolidineacetic acid
alpha-Methyl 5-[[3,4-bis(phenylmethoxy)phenyl]methylene]-4-oxo-2-thioxo-3-thiazolidineacetic acid
alpha-Phenylmethyl 5-[[3,4-bis(phenylmethoxy)phenyl]methylene]-4-oxo-2-thioxo-3-thiazolidineacetic acid
5-[1-[3-Methoxy-4-(phenylmethoxy)phenyl]ethylidene]-4-oxo-2-thioxo-3-thiazolidineacetic acid.

All preferred features of the first, second and third aspects of the invention also apply to the fourth aspect.

The fifth aspect of the invention provides a method of preparing the novel compounds of the third aspect or fourth aspect of the invention.

The compounds of this invention can be prepared by condensation of rhodanine-3-acetic acid, or 2,4-dioxo-3-thiazolidineacetic acid or an analogue or derivative thereof, with the appropriate substituted benzaldehyde derivative (or benzophenone derivative) under general acid-base catalysis conditions using typical reagents for such a process, e.g. sodium acetate in acetic acid or ammonium acetate in a suitable solvent such as toluene, usually with the application of heat and preferably at the reflux temperature of the solvent (Schemes 1 and 2).

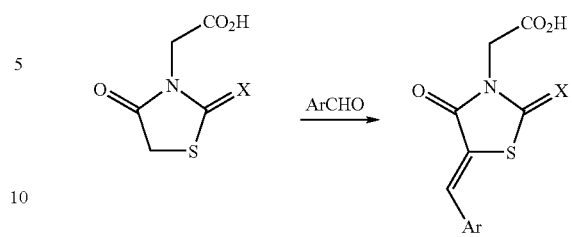

Scheme 1

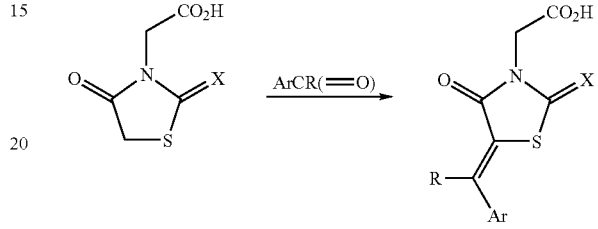

Scheme 2

Rhodanine-3-acetic acid, oxo-rhodanine-3-acetic acid and the benzaldehyde derivatives are either commercially available, can readily be prepared or are synthesised by the methods outlined in the Examples.

A compound of general formula (I) may be transformed into another compound of general formula (I) using methods well known to those skilled in the art. If protection of a particular functional group is required, this can be achieved using protecting groups and conditions known in the art. The protecting groups may be removed at any stage in the synthesis of the compounds of formula I or may be present on the final compound of formula I.

All preferred features of the first, second, third and fourth aspects of the invention also apply to the fifth aspect.

The sixth aspect of the invention provides a pharmaceutical composition comprising a compound of the third aspect or fourth aspect of the invention. The pharmaceutical formulation will provide a compound of the third or fourth aspect of the invention and a pharmaceutically acceptable carrier.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions).

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3 (6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulisers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilised) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used. This dosage may be repeated as often as appropriate. If side effects develop the amount and/or frequency of the dosage can be reduced, in accordance with normal clinical practice. The likely dosage of the substance is at an effective dosage of 0.1–750 milligrams/kg/day, preferably 0.1–10 milligrams/kg/day.

It should be understood that in addition to the ingredients particularly mentioned above, the formulations may also include other agents conventional in the art having regard to the type of formulation in question, for example those suitable for oral administration may contain flavouring agents.

All preferred features of the first, second, third, fourth and fifth aspects of the invention also apply to the sixth aspect.

The seventh aspect of the invention provides the compounds of the third and fourth aspects or the pharmaceutical compositions of the sixth aspect of the invention for use in medicine.

The compounds of the invention may be used in combination with one or more other antifungal agents.

In particular, the compounds of the formula (I) and their salts are provided for use as anti-fungal agents. These compounds are useful in the curative or prophylactic treatment of fungal infections in animals including humans. For example, they are useful in treating topical fungal infections in man caused by, among other organisms, species of *Candida, Trichophyton, Microsporum* or *Epidermophyton,* or in mucosal infections caused by *Candida albicans* (e.g. thrush and vaginal candidiasis). They can also be used in the treatment of systemic fungal infections caused by, for example, species of *Candida* (e.g. *Candida albicans*), *Cryptococcus neoformans, Aspergillus flavus, Aspergillus fumigatus, Coccidioides, Paracoccidioides, Histoplasma* or *Blastomyces*.

All preferred features of the first, second, third, fourth, fifth and sixth aspects of the invention also apply to the seventh aspect.

The invention will now be illustrated by reference to the following non-limiting examples.

EXAMPLES

Synthetic Methods

Example 1

3-Hydroxy-4-pentyloxybenzaldehyde

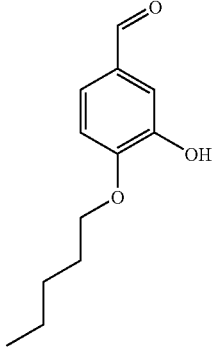

n-Bromopentane (0.90 mL, 7.25 mmol, 1 eq) was added dropwise to a stirred solution of 3,4-dihydroxybenzaldehyde (1 g, 7.25 mmol, 1 eq) and cesium carbonate (7.07 g, 21.7 mmol, 3 eq) in N,N-dimethylformamide. The reaction mixture was stirred overnight and concentrated in vacuo. The residue was dissolved in ethyl acetate (50 mL), and the organic solution washed with water (2×50 mL), and brine (50 mL), then dried over magnesium sulfate and evaporated. Chromatography on silica with dichloromethane:petroleum ether (4:1) as eluent gave the product as a brown oil (367 mg, 24%). $^1$H NMR (CDCl$_3$) δ 9.79 (s, 1H, O═C—H), 6.21 (s, 1H, OH), 4.08 (t, 2H, OCH$_2$), 1.81 (m, 2H, OCH$_2$CH$_2$), 1.40 (m, 4H, CH$_2$CH$_2$CH$_3$), 0.89 (t, 3H, CH$_3$).

Example 2

3-Hydroxy-4-[(4-methoxyphenyl)methoxy]benzaldehyde

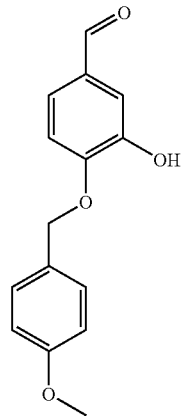

4-Methoxybenzylchloride (20.6 mL, 0.14 mol, 1.05 eq) was added to a stirred solution of 3,4-dihydroxybenzaldehyde (20 g, 0.15 mol, 1 eq), tetra-n-butylammonium iodide (44.6 g, 0.12 mol, 0.8 eq) and cesium carbonate (35.4 g, 0.11 mol, 0.75 eq) in N,N-dimethylformamide (200 mL). The reaction mixture was stirred for 2 days, and then concentrated in vacuo. The residual solution was diluted with ethyl acetate (200 mL) and washed with 0.5M HCl (400 mL), water (4×200 mL) and saturated sodium chloride solution (200 mL), then dried over sodium sulfate and evaporated in vacuo. This gave a gummy solid which was recrystallized from ethyl acetate and petroleum ether to give the product as a pale brown powder (21.29 g, 57%). $^1$H NMR (CDCl$_3$) δ 9.84 (s, 1H, O═C—H), 5.80 (s, 1H, OH), 5.13 (s, 2H, CH$_2$Ar), 3.85 (s, 3H, OCH$_3$).

Example 3

4-[(4-Methoxyphenyl)methoxy]-3-(phenylmethoxy)benzaldehyde

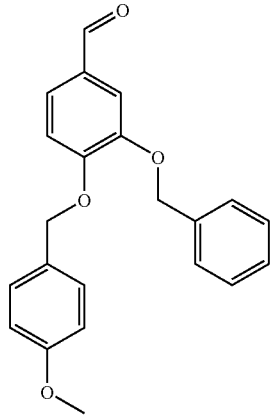

Benzyl bromide (13.56 mL, 0.11 mol, 1.1 eq) was added to a solution of 3-hydroxy-4-[(4-methoxyphenyl)methoxy] benzaldehyde (26.91 g, 0.10 mL, 1 eq) and cesium carbonate (20.37 g, 0.06 mol, 0.6 eq) in N,N-dimethylformamide (150 mL). The reaction mixture was stirred overnight and then concentrated in vacuo. The residual solution was diluted with ethyl acetate (200 mL) and washed with water (200 mL), saturated sodium chloride solution (3×200 mL), and 0.5M aqueous sodium hydroxide (3×200 mL), then dried over sodium sulfate and evaporated in vacuo. This gave a gummy solid which was recrystallized from ethyl acetate and petroleum ether to give the product as a pale brown powder (25.93 g, 71%). $^1$H NMR (CDCl$_3$) δ 9.81 (s, 1H, O═C—H), 5.21 (s, 2H, CH$_2$Ar), 5.20 (s, 2H, CH$_2$Ar), 3.84 (s, 3H, OCH$_3$).

Example 4

4-Hydroxy 3-(phenylmethoxy)benzaldehyde

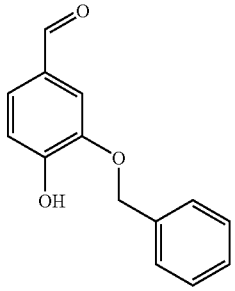

A solution of 4-[(4-Methoxyphenyl)methoxy]-3-(phenylmethoxy)benzaldehyde (25.93 g, 0.074 mol) in acetic acid (200 mL) was heated to reflux (150°C) and stirred for 2 days. The reaction mixture was concentrated in vacuo and the residue dissolved in ethyl acetate (200 mL). The organic solution was washed with water (200 mL) and 0.5M aqueous sodium hydroxide (5×200 mL). The basic extracts were combined, acidified to pH 1 with concentrated HCl and back extracted with ethyl acetate (2×300 mL). The organic solution was dried over sodium sulfate and evaporated in vacuo to a gummy solid, which was recrystallized from ethyl acetate and petroleum ether to give the product as a pale brown powder (14 g, 82%). $^1$H NMR (CDCl$_3$) δ 9.84 (s, 1H, O═C—H), 6.26 (1H, s, OH), 5.20 (s, 2H, CH$_2$Ph).

Example 5

3-(Hydroxymethyl)-4-(2-phenylethoxy)benzaldehyde

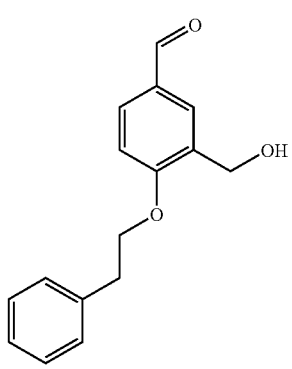

(2-Bromoethyl)benzene (4.38 g, 23.7 mmol, 3 eq) was added to a stirred solution of 3-(hydroxymethyl)-4-hydroxybenzaldehyde (1.2 g, 7.9 mmol, 1 eq) and tetra-n-butylammonium iodide (2.91 g, 7.9 mmol, 1 eq) in N,N-dimethylformamide (10 mL). To the solution was added cesium carbonate (5.14 g, 15.8 mmol, 2 eq) and the reaction mixture stirred overnight. It was partitioned between ethyl acetate (100 mL) and water (100 mL), and the two layers separated. The organic layer was washed with water (2×100 mL), saturated aqueous sodium bicarbonate (100 mL), then water again (100 mL), dried over sodium sulfate and evaporated. The residue was purified by chromatography on silica gel; elution with dichloromethane:diethyl ether (5:1) gave the product as a colourless oil (1.07 g, 53%). $R_F$ (petroleum ether:diethyl ether, 3:1) 0.50. $^1$H NMR (CDCl$_3$) δ 9.84 (s, 1H, O=C—H), 7.88 (s, 1H, ArH), 7.79 (dd, 1H, J 8.4 and 1.3 Hz, ArH), 6.95 (d, 1H, J 8.7 Hz, ArH), 4.70 (s, 2H, CH$_2$OH), 4.31 (t, 2H, J 6.2 Hz, OC$\underline{H}_2$CH$_2$Ph), 3.17 (t, 2H, J 6.2 Hz, OCH$_2$C$\underline{H}_2$Ph), 3.06 (s, 1H, OH).

Example 6

3-(Phenylmethoxy)-4-[(4-trifluoromethylphenyl)methoxy]benzaldehyde

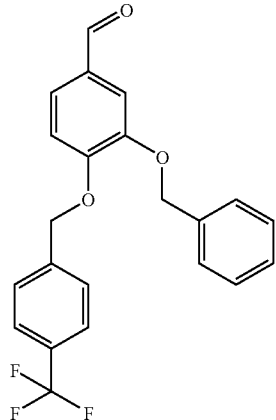

4-Trifluoromethylbenzyl bromide (0.17 mL, 1.09 mmol, 1 eq) was added dropwise to a stirred solution of 3-benzyloxy-4-hydroxybenzaldehyde (250 mg, 1.09 mmol, 1 eq) and cesium carbonate (357 mg, 1.09 mmol, 1 eq) in N,N-dimethylformamide (10 mL). The reaction mixture was stirred overnight, then diluted with ethyl acetate (30 mL) and washed sequentially with water (4×30 mL), 0.5M aqueous sodium hydroxide (30 mL), 10% HCl and brine. The organic solution was dried over sodium sulfate and evaporated in vacuo to give the product as a white powder (422 mg, 99%). $^1$H NMR (CDCl$_3$) δ 9.82 (s, 1H, O=C—H), 5.28 (2H, s, CH$_2$Ar), 5.21 (s, 2H, CH$_2$Ph).

The following aldehydes were also made by this method:
4-(2-Phenylethoxy)-3-(phenylmethoxy)benzaldehyde
4-[(3,4-Difluorophenyl)methoxy]-3-(phenylmethoxy)benzaldehyde
3-(Phenylmethoxy)-4-[(3-trifluoromethylphenyl)methoxy]benzaldehyde
4-[(2,4-Difluorophenyl)methoxy]-3-(phenylmethoxy)benzaldehyde
4-[(4-Methylsulfonylphenyl)methoxy]-3-(phenylmethoxy)benzaldehyde
3-(Phenylmethoxy)-4-[(4-trifluoromethoxyphenyl)methoxy]benzaldehyde
4-[(4-Methylphenyl)methoxy]-3-(phenylmethoxy)benzaldehyde
4-[(4-Chlorophenyl)methoxy]-3-(phenylmethoxy)benzaldehyde
4-[(2-Pyridyl)methoxy]-3-phenylmethoxybenzaldehyde
3-Phenylmethoxy-4-[[3,5-bis(trifluoromethyl)phenyl]methoxy]benzaldehyde
3-(Phenylmethoxy)-4-(2-cyclohexylethoxy)benzaldehyde Example 7

3-Hydroxy-4-(phenylmethoxy)benzaldehyde

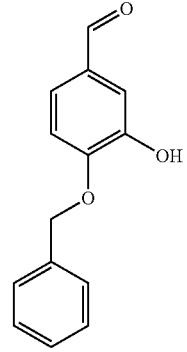

Benzyl bromide (9 mL, 0.073 mol, 1.05 eq) was added to a stirred solution of 3,4-dihydroxybenzaldehyde (10 g, 0.07 mol, 1 eq), tetra-n-butylammonium iodide (29.4 g, 0.077 mol, 1.1 eq) and cesium carbonate (24.8 g, 0.073 mol, 1.05 eq) in N,N-dimethylformamide (200 mL). The reaction mixture was stirred overnight, and then concentrated in vacuo. The residual solution was diluted with ethyl acetate (200 mL) and washed with water (2×200 mL). The organic solution was then extracted with 0.5M aqueous sodium hydroxide (5×200 mL), and the basic extracts combined and washed with ethyl acetate (400 mL), then acidified to pH 1 with concentrated HCl and back extracted with ethyl acetate (2×300 mL). The organic extracts were combined, washed with brine (200 mL), dried over sodium sulfate and evaporated in vacuo. This gave a gummy solid, which was recrystallized from ethyl acetate and petroleum ether to give the product as a brown powder (8.4 g, 51%). $^1$H NMR (CDCl$_3$) δ 9.84 (s, 1H, O=C—H), 5.84 (s, 1H, OH), 5.21 (s, 2H, CH$_2$Ph).

Example 8

3-Hydroxy-4-(2-phenylethoxy)-benzaldehyde

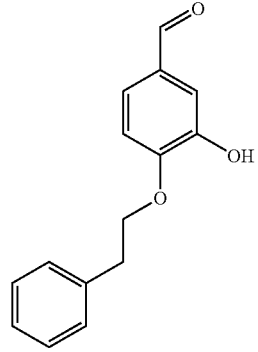

(2-Bromoethyl)benzene (20 mL, 0.14 mol, 2 eq) was added to a stirred solution of 3,4-dihydroxybenzaldehyde (10 g, 0.072 mol, 1 eq), tetra-n-butylammonium iodide (27 g, 0.072 mol, 1 eq) and cesium carbonate (14.2 g, 0.043 mol, 0.6 eq) in N,N-dimethylformamide (50 mL). The solution was stirred overnight, then concentrated in vacuo and diluted with ethyl acetate (200 mL). The organic solution was washed with 1M HCl (2×200 mL), and brine (200 mL), dried over sodium sulfate and evaporated. The residue was purified by chromatography on silica gel, eluting with toluene:ethyl acetate (19:1). This gave the product as a colourless oil which crystallized on standing (2.71 g, 15%). $R_F$ (toluene:ethyl acetate, 9:1) 0.31. $^1$H NMR (CDCl$_3$) δ 9.84 (s, 1H, O=C—H), 6.96 (d, 1H, J 8.3 Hz, ArH), 5.64 (s, 1H, OH), 4.36 (t, 2H, J 7.2 Hz, OCH$_2$CH$_2$Ph), 3.17 (t, 2H, J 7.2 Hz, OCH$_2$CH$_2$Ph).

Example 9

3-[(2-Pyridyl)methoxy]-4-(2-phenylethoxy)benzaldehyde

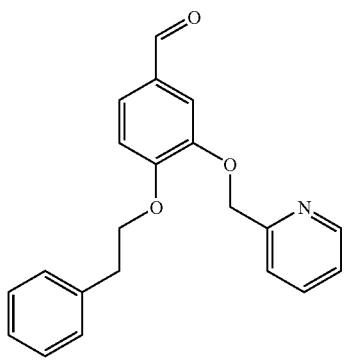

Cesium carbonate (800 mg, 2.5 mmol, 2 eq) was added to a stirred solution of 3-hydroxy-4-(2-phenylethoxy)-benzaldehyde (300 mg, 1.24 mmol, 1 eq), 2-picolyl chloride (210 mg, 1.3 mmol, 1.05 eq) and tetra-n-butylammonium iodide (460 mg, 1.24 mmol, 1 eq) in N,N-dimethylformamide (10 mL). The solution was stirred overnight, then concentrated in vacuo. The residue was azeotroped with water (2×10 mL), toluene (2×10 mL) and then purified by chromatography on silica gel. Elution with petroleum ether:ethyl acetate (1:1) gave the product as a white powder (367 mg, 89%). $^1$H NMR (CDCl$_3$) δ 9.75 (s, 1H, O=C—H), 8.55 (d, 1H, J 4.9 Hz, pyH), 7.66 (ddd, 1H, J 7.5, 7.5 and 1.9 Hz, PyH), 7.47 (d, 1H, J 7.5 Hz, ArH), 5.22 (s, 2H, OCH$_2$Py), 4.27 (t, 2H, J 7.2 Hz, OCH$_2$CH$_2$Ph), 3.15 (t, 2H, J 7.2 Hz, OCH$_2$CH$_2$Ph).

Example 10

3-(1-Phenyl-2,2,2-trifluoroethoxy)-4-(2-phenylethoxy)benzaldehyde

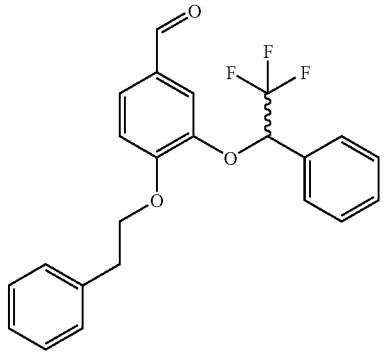

Cesium carbonate (242 mg, 0.74 mmol, 0.6 eq) was added to a stirred solution of 3-hydroxy-4-(2-phenylethoxy)-benzaldehyde (300 mg, 1.24 mmol, 1 eq) and 2,2,2-trifluoro-1-phenylethyltrifluoromethanesulfonate—(420 mg, 1.36 mmol, 1.1 eq) in N,N-dimethylformamide (5 mL). The reaction mixture was stirred for 2 days and then partitioned between diethyl ether (50 mL) and water (50 mL), and the two layers separated. The organic layer was washed with water (3×50 mL), brine (50 mL), dried over sodium sulfate and evaporated. The residue was purified by chromatography on silica gel. Elution with petroleum ether:diethyl ether (3:1) gave the product as a gummy solid which was recrystallized from diethyl ether to give white granular crystals (183 mg, 37%). $R_F$ (petroleum ether:diethyl ether, 3:1) 0.20. $^1$H NMR (CDCl$_3$) δ 9.63 (s, 1H, O=C—H), 6.84 (d, 1H, J 8.4 Hz, ArH), 5.42 (q, 1H, J 6.2 Hz, CHCF$_3$), 4.19 (t, 2H, J 6.5 Hz, OCH$_2$CH$_2$Ph), 3.05 (t, 2H, J 6.5 Hz, OCH$_2$CH$_2$Ph).

The following aldehydes were prepared via a similar procedure:

(R)-3-(1-Phenyl-2,2,2-trifluoroethoxy)-4-[2-phenylethoxy]benzaldehyde (S)-3-(1-Phenyl-2,2,2-trifluoroethoxy)-4-[2-phenylethoxy]benzaldehyde Example 11

3-[(S)-1-Phenyl-2,2,2-trifluoroethoxy]-4-[(4-methoxyphenyl)methoxy]benzaldehyde

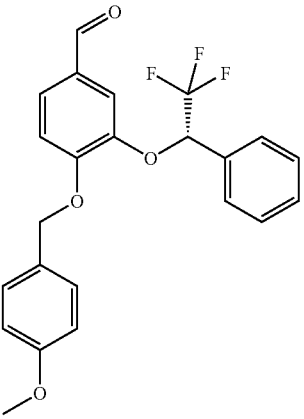

(R)-(−)-2,2,2-Trifluoro-1-phenylethyltrifluoromethanesulfonate (3.08 g, 0.01 mol, 1 eq) was added to a stirred solution of 3-hydroxy-4-[(4-methoxyphenyl)methoxy]-benzaldehyde (2.58 g, 0.01 mol, 1 eq) and cesium carbonate (3.26 g, 0.01 mol, 1 eq) in N,N-dimethylformamide (20 mL). The solution was stirred for 48 h, diluted with ethyl acetate (100 mL) and washed with 1M HCl (3×200 mL), brine (200 mL), 1M sodium hydroxide (4×200 mL), and brine (200 mL), then dried over sodium sulfate and evaporated. The residue was purified by chromatography on silica gel, using petroleum ether:ethyl acetate (5:1) as eluent, to give the product as a yellow oil which crystallized on standing to give a cream coloured powder (2.08 g, 50%). $R_F$ (dichloromethane) 0.77. $^1$H NMR (CDCl$_3$) □ 9.77 (s, 1H, O=C—H), 7.06 (d, 1H, J 8.3 Hz, ArH), 5.52 (q, 1H, J 6.0 Hz, CHCF$_3$), 5.13 (s, 2H, OCH$_2$Ph), 3.84 (s, 3H, OCH$_3$).

Example 12

3-(Phenylmethoxy)-4-(2,2,3,3,3-pentafluoropropoxy)benzaldehyde

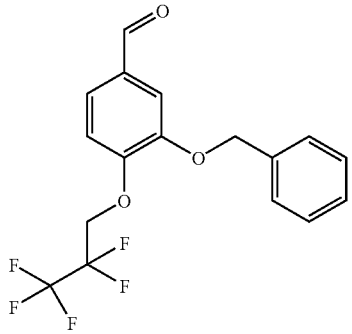

Trifluoromethane sulfonic anhydride (0.67 mL, 4.0 mmol, 1.2 eq) was added dropwise to a solution of 2,2,3,3,3-pentafluoro-1-propanol (500 mg, 3.33 mmol, 1 eq) and di-iso-propylethylamine (1.45 mL, 8.33 mmol, 2.5 eq) in dichloromethane (5 mL) at −60°C. The solution was allowed to warm to −30°C and stirred for 15 min. It was then poured into a separating funnel and washed with 1M HCl (2×50 mL), and brine (50 mL). The dichloromethane solution was added directly to a stirred solution of 3-(phenylmethoxy)-4-hydroxybenzaldehyde (1.14 g, 5.0 mmol, 1.5 eq) and cesium carbonate (1.09 g, 3.33 mmol, 1 eq) in N,N-dimethylformamide (15 mL). The reaction mixture was stirred overnight, diluted with ethyl acetate (100 mL) and washed with 1 M HCl (2×200 mL), brine (200 mL), 1M sodium hydroxide (4×200 mL) and brine (200 mL). The organic solution was dried over sodium sulfate and evaporated. The residue was purified by column chromatograghy on silica gel and elution with dichloromethane gave the product as a colourless oil (850 mg, 74%). $R_F$ (dichloromethane) 0.72. $^1$H NMR (CDCl$_3$) δ 9.89 (s, 1H, O═C—H), 7.55 (d, 1H, J 1.9 Hz, ArH), 7.10 (d, 1H, J 8.3 Hz, ArH), 5.20 (s, 2H, OCH$_2$Ph), 4.56 (td, 2H, J 12.4 and 1.1 Hz, OCH$_2$CF$_2$).

Example 13

3-[(S)-1-phenyl-2,2,2-trifluoroethoxy]-4-hydroxybenzaldehyde

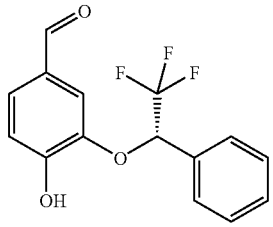

A solution of 3-[(S)-1-phenyl-2,2,2-trifluoroethoxy]-4-[(4-methoxyphenyl)methoxy]-benzaldehyde (2.08 g, 0.005 mol) in acetic acid (25 mL) was heated to 150°C. and stirred for 72 h. It was then cooled to room temperature and concentrated in vacuo. The residue was diluted with ethyl acetate (100 mL), and the organic solution washed with water (100 mL) and extracted with 1M sodium hydroxide (5×100 mL). The basic extracts were combined and acidified to pH 1 with concentrated HCl, then extracted with ethyl acetate (2×100 mL). The organic extracts were combined, dried over sodium sulfate and evaporated. The residue was purified by chromatography on silica gel and elution with petroleum ether:ethyl acetate (6:1) gave the product as a colourless oil, which later crystallised to a white powder (1.14 g, 80%). $R_F$ (dichloromethane) 0.53. $^1$H NMR (CDCl$_3$) 9.71 (s, 1H, O═C—H), 7.09 (d, 1H, J 8.3 Hz, ArH), 6.39 (s, 1H, OH), 5.50 (q, 1H, J 6.0 Hz, CHCF$_3$).

Example 14

3-[(S)-1-Phenyl-2,2,2-trifluoroethoxy]-4-[(R)-2-phenylpropoxy]-benzaldehyde

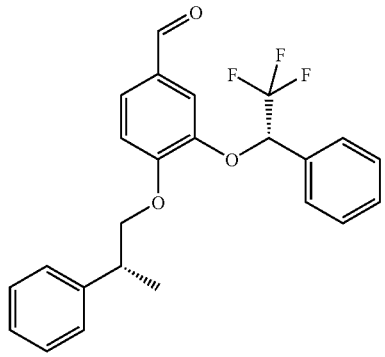

This compound was prepared from methane (R)-2-phenylpropyl sulfonate (130 mg, 0.9 eq) and 3-[(S)-1-phenyl-2,2,2-trifluoroethoxy]-4-hydroxybenzaldehyde (200 mg, 1 eq) using the same procedure as outlined in Example 28, except that the reaction required 2 days. The product was purified by column chromatography on silica gel, with petroleum ether: ethyl acetate (9:1) as eluent, and was obtained as a colourless oil (120 mg, 43%). $R_F$ (petroleum ether:ethyl acetate, 4:1) 0.57. $^1$H NMR (CDCl$_3$) 9.74 (s, 1H, O═C—H), 6.95 (d, 1H, J 8.3 Hz, ArH), 5.48 (q, 1H, J 6.4 Hz, CHCF$_3$), 4.18 (dd, 1H, J 9.0 and 6.4 Hz, CH$_2$CHCH$_3$Ph), 4.11 (dd, 1H, J 9.0 and 7.2 Hz, CH$_2$CHCH$_3$Ph), 3.32 (m, 1H, CH$_2$CHCH$_3$Ph), 1.44 (d, J 6.8 Hz, CH$_2$CHCH$_3$Ph): $^{19}$F NMR (CDCl$_3$) −76.73.

Example 15

3-[(S)-1-Phenyl-2,2,2-trifluoroethoxy]-4-[(S)-2-phenylpropoxy]benzaldehyde

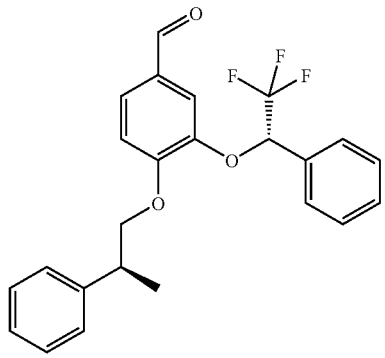

This compound was prepared from methane (S)-2-phenylpropyl sulfonate (1.56 g, 1 eq) using the same procedure as outlined in Example 14, except that the reaction required 20 h. The product was purified by chromatography on silica gel, with toluene:ethyl acetate (97:3) as eluent, and was obtained as a colourless oil (11.0 g, 46%). $R_F$ (petroleum ether:ethyl acetate, 4:1) 0.57. $^1$H NMR (CDCl$_3$) δ 9.73 (s, 1H, O═C—H), 6.95 (d, 1H, J 8.3 Hz, ArH), 5.43 (q, 1H, J 6.4 Hz, CHCF$_3$), 4.20 (dd, 1H, J 9.0 and 7.2 Hz, CH₂CHCH₃Ph), 4.14 (dd, 1H, J 9.0 and 6.4 Hz, CH₂CHCH₃Ph), 3.35 (m, 1H, CH₂CHCH₃Ph), 1.47 (d, J 7.2 Hz, CH₂CHCH₃Ph): ¹⁹F NMR (CDCl₃) −76.67.

Example 16

3-(1-Phenylethoxy)-4-(2-phenylethoxy)-benzaldehyde

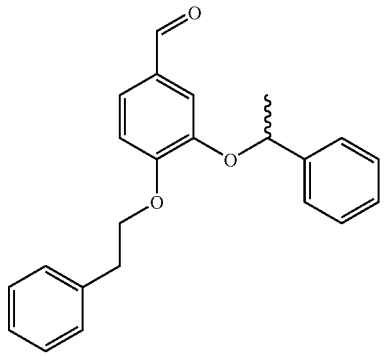

(1-Bromoethyl)benzene (0.56 mL, 4.13 mmol, 2 eq) was added to a stirred solution of 3-hydroxy-4-(2-phenylethoxy)-benzaldehyde (500 mg, 2.06 mmol, 1 eq) and cesium carbonate (672 mg, 2.06 mmol, 1 eq) in N,N-dimethylformamide (8 mL). The solution was stirred overnight and then diluted with ethyl acetate (50 mL). The organic solution was washed with 1M HCl (2×100 mL), and brine (100 mL), dried over sodium sulfate and evaporated. The residue was purified by chromatography on silica gel and elution with petroleum ether:ethyl acetate (6:1) gave the product as a colourless oil (680 mg, 95%). R_F (petroleum ether:ethyl actetate, 4:1) 0.51. ¹H NMR (CDCl₃) δ 9.72 (s, 1H, O=C—H), 6.93 (d, 1H, J 7.9 Hz, ArH), 5.38 (q, 1H, J 6.4 Hz, CHCH₃Ph), 4.33 (m, 2H, CH₂CH₂Ph), 3.21 (t, 2H, J 6.8 Hz, CH₂CH₂Ph), 1.67 (d, 3H, J 6.4 Hz, CHCH₃Ph).

Example 17

3-[(1-Phenyl-2-hydroxy)ethoxy]-4-(2-phenylethoxy)-benzaldehyde

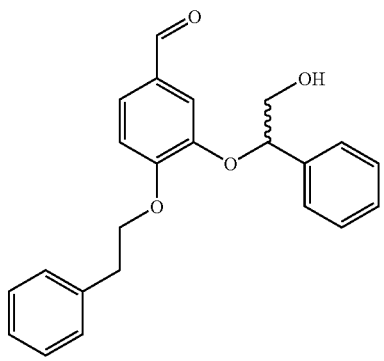

(2-Acetoxy-1-bromoethyl)benzene (3.32 g, 13.67 mmol, 1.2 eq) was added to a stirred solution of 3-hydroxy-4-(2-phenylethoxy)-benzaldehyde (2.76 g, 11.39 mmol, 1 eq) and cesium carbonate (2.97 g, 9.11 mmol, 0.8 eq) in N,N-dimethylformamide (15 mL). The solution was stirred for 19 hours at room temperature, then 21 hours at 80° C. The reaction was worked up by partitioning between ethyl acetate and water (brine was added to help break up the emulsion that formed). The organic layer was washed twice more with water, brine and then dried over sodium sulfate and evaporated to give a dark oil. The residue was purified by chromatography on silica gel and elution with diethyl ether gave an orange oil. This oil was dissolved in methanol (100 ml) and to the solution was added an aqueous solution of sodium hydroxide (7 ml, 1M). After 30 minutes the mixture was evaporated (to remove the methanol) and the residue partitioned between dichloromethane and water. The organic layer was dried over sodium sulfate and evaporated. The residue was purified by chromatographed on silica gel and elution with petroleum ether:diethyl ether (1:2) gave the product as a cream coloured powder (2.1 g, 50%). R_F (petroleum ether:ethyl actetate, 1:1) 0.45. ¹H NMR (CDCl₃) δ 9.67 (s, 1H, O=C—H), 6.93 (d, 1H, J 8.3 Hz, ArH), 5.29 (m, 1H, CHCH₂OH), 4.31 (t, 2H, J 6.8 Hz, CH₂CH₂Ph), 4.01 (m, 1H, CH₂OH), 3.85 (m, 1H, CH₂OH), 3.22 (t, 2H, J 6.8 Hz, CH₂CH₂Ph).

Example 18

Methyl 2-(2-phenylmethoxy-5-formyl)phenoxy-2-phenylacetate

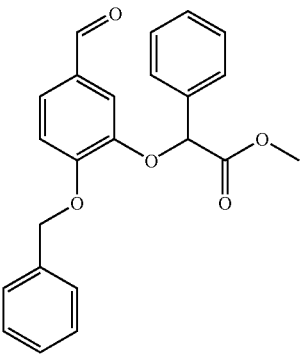

Methyl alpha-bromophenylacetate (5.3 g, 0.023 mol, 1.05 eq) was added to a solution of 3-hydroxy-4-(phenylmethoxy)benzaldehyde (5 g, 0.022 mol, 1 eq) and cesium carbonate (7.9 g, 0.024 mol, 1.1 eq) in N,N-dimethylformamide (100 mL) and the reaction mixture stirred overnight. The reaction mixture was diluted with ethyl acetate (100 mL) and washed with water (200 mL), 0.5M aqueous sodium hydroxide (200 mL) and brine (200 mL). The organic solution was dried over sodium sulfate and evaporated in vacuo to give the product as a brown oil (7.5 g, 91%). ¹H NMR (CDCl₃) δ 9.80 (s, 1H, O=C—H), 5.74 (s, 1H, CHPh), 5.25 (s, 2H, CH₂Ph), 3.70 (s, 3H, CH₃). HPLC-MS: found 375 (APCI−), 377 and 399 (APCI+). calcd for C₂₃H₂₀O₅ (M+) 376.

The following aldehydes were prepared by a similar procedure:
4-Phenylmethoxy-3-[(2-pyridyl)methoxy]benzaldehyde
3-[(4-Methylsulfonylphenyl)methoxy]-4-phenylmethoxybenzaldehyde
3-[(3,4-Difluorophenyl)methoxy]-4-phenylmethoxybenzaldehyde

Example 19

Methyl 2-(2-[(2-phenylethyoxy)]-5-formyl)phenyloxy-2-phenylacetate

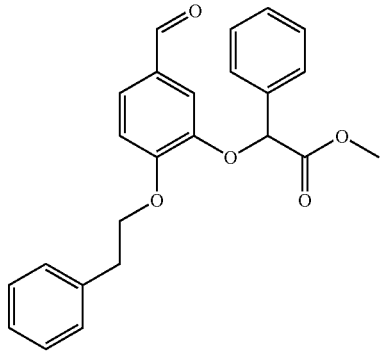

Methyl α-bromophenyl acetate (1.3 mL, 8.69 mmol, 1.05 eq) was added to a stirred solution of 3-hydroxy-4-(2-phenylethoxy)benzaldehyde (2 g, 8.26 mmol, 1 eq) and cesium carbonate (2.95 g, 9.08 mmol, 1.1 eq) in N,N-dimethylformamide (30 mL). The solution was stirred over 3 days and then partitioned between ethyl acetate (100 mL) and water (200 mL). The separated organic layer was washed with brine (3×200 mL), dried over sodium sulfate and evaporated, to give the crude product. This was not purified further and taken immediately onto the next step. $R_F$ (petroleum ether:ethyl acetate, 3:1) 0.50.

Example 20

2-[2-(2-Phenylethoxy)-5-formyl]phenoxy-2-phenylacetic acid

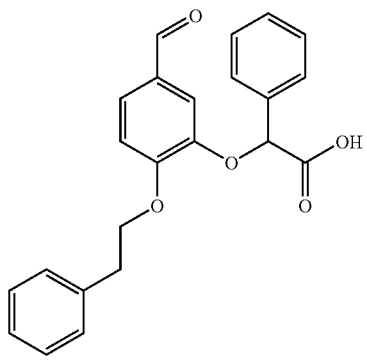

Lithium hydroxide (460 mg, 19.2 mmol, 3 eq) in water (10 mL) was added to a solution of methyl 2-(2-[2-phenylethoxy]-5-formyl)phenyloxy-2-phenylacetate (2.5 g, 6.4 mmol, 1 eq) in tetrahydrofuran (30 mL). This formed a two-phase mixture, so methanol (10 mL) was added and the resulting one-phase solution was stirred overnight, before concentration in vacuo. The residue was partitioned between ethyl acetate (100 mL) and 1M HCl (200 mL), and the two layers separated. The organic layer was washed with water (200 mL), dried over sodium sulfate, and evaporated to leave the product, which was recrystallized from ethyl acetate and petroleum ether to give a cream coloured powder (2.4 g, 99% (2 steps)). $^1$H NMR (CDCl$_3$) δ 11.04 (broad s, 1H, CO$_2$H), 9.68 (s, 1H, O=C—H), 6.91 (d, 1H, J 8.7 Hz, ArH), 5.76 (s, 1H, OCHPh), 4.26 (m, 2H, OCH$_2$CH$_2$Ph), 3.14 (t, 2H, J 6.9 Hz, OCH$_2$CH$_2$Ph).

Example 21

2-(2-Phenylmethoxy-5-formyl)phenoxy-2-phenylacetic acid

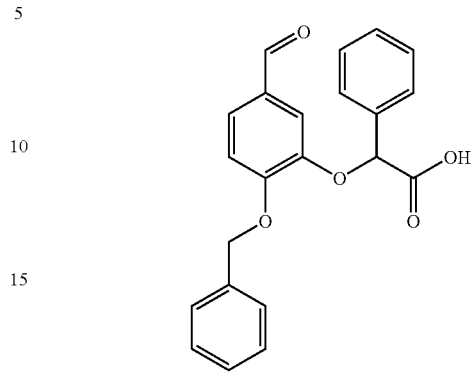

Lithium hydroxide (1.4 g, 0.06 mol, 3 eq) in water (10 mL) was added to a solution of methyl 2-(2-phenylmethoxy-5-formyl)phenyloxy-2-phenylacetate (7.5 g, 0.02 mol, 1 eq) in tetrahydrofuran (50 mL). The reaction mixture was stirred for 3 days and then concentrated in vacuo to remove the tetrahydrofuran. The aqueous solution was washed with ethyl acetate (20 mL), then acidified to pH 1 with concentrated HCl and extracted with ethyl acetate (2×20 mL). The organic extracts were combined, washed with water (2×20 mL) and brine (20 mL), dried over sodium sulfate and evaporated in vacuo. This gave a gummy solid which was recrystallized from ethyl acetate and petroleum ether to give the product as cream coloured needles (5.36 g, 74%). $^1$H NMR (CDCl$_3$) δ 9.70 (s, 1H, O=C—H), 5.61 (s, 1H, CHPh), 5.17 (s, 2H, CH$_2$Ph).

Example 22

N,N-Di-n-propyl-2-(2-phenylmethoxy-5-formyl)phenoxy-2-phenylacetamide

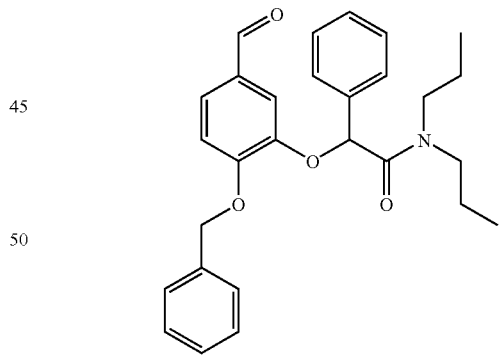

Di-n-propylamine (0.28 g, 2.76 mmol, 2 eq) was added to a solution of 2-(2-phenylmethoxy-5-formyl)phenyloxy-2-phenylacetic acid (0.50 g, 1.38 mmol, 1 eq), 1-hydroxy-7-azabenzotriazole (0.38 g, 2.76 mmol, 2 eq), and N-methylmorpholine (0.42 mL, 3.77 mmol, 2.73 eq) in N,N-dimethylformamide (10 mL). To this was added 1-(3-dimethylaminopropyl)-3-ethylcarbodiimide hydrochloride (0.75 g, 3.9 mmol, 2 eq) and the reaction mixture was stirred overnight. The reaction mixture was diluted with ethyl acetate (20 mL) and washed sequentially with 10% HCl (3×20 mL), brine (20 mL), saturated aqueous sodium bicarbonate (2×20 mL) and brine (20 mL). The organic solution was dried over sodium sulfate and evaporated in vacuo to give the product as a pale brown oil (0.60 g, 97%). $^1$H NMR (CDCl$_3$) δ 9.80 (s, 1H, O=C—H), 6.00 (s, 1H, CHPh), 5.28 (2×d, 2H, CH$_2$Ph), 3.23 (m, 4H, N[CH$_2$]$_2$), 1.50 (m, 2H, CH$_2$CH$_3$), 1.29 (m, 2H, CH$_2$CH$_3$), 0.81 (t, 3H, CH$_2$CH$_3$), 0.67 (t, 3H, CH$_2$CH$_3$).

N-(2-Phenyl)ethyl-2-(2-phenylmethoxy-5-formyl)phenoxy-2-phenylacetamide;

N-Benzyl-2-(2-phenylmethoxy-5-formyl)phenoxy-2-phenylacetamide

N-Phenyl-2-(2-phenylmethoxy-5-formyl)phenoxy-2-phenylacetamide

2-Ethylpiperidinyl-2-(2-phenylmethoxy-5-formyl)phenoxy-2-phenylacetamide

N-Propyl-2-(2-phenylmethoxy-5-formyl)phenoxy-2-phenylacetamide

Cis-2,6-Dimethylmorpholinyl-2-(2-phenylmethoxy-5-formyl)phenoxy-2-phenylacetamide N,N-Di-n-butyl-2-(2-phenylmethoxy-5-formyl)phenoxy-2-phenylacetamide N-n-Propyl-N-sec-butyl-2-(2-phenylmethoxy-5-formyl)phenoxy-2-phenylacetamide were also prepared by this method.

Example 23

N,N-Di-n-propyl-2-(2-(2-phenylethoxy)-5-formyl)phenoxy-2-phenylacetamide

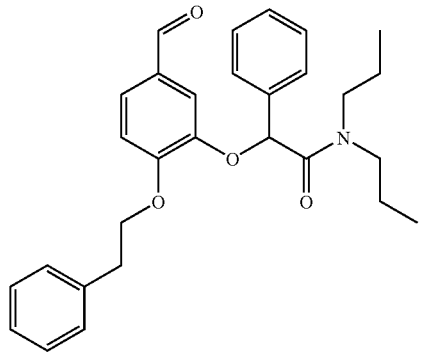

This compound was prepared from 2-[2-(2-phenylethoxy)-5-formyl]phenoxy-2-phenylacetic acid (550 mg, 1 eq) using the procedure described in Example 9, except that the reaction was stirred for 3 days. The product was purified by chromatography on silica gel, with petroleum ether:ethyl acetate (1:1) as eluent, and was obtained as a colourless oil (600 mg, 89%). $^1$H NMR (CDCl$_3$) 9.81 (s, 1H, O=C—H), 6.99 (d, 1H, J 8.1 Hz, ArH), 5.98 (s, 1H, OCHPh), 4.31 (m, 2H, m, OCH$_2$CH$_2$Ph), 3.29 (4H, m, 2×NCH$_2$), 3.16 (2H, t, J 6.9 Hz, OCH$_2$CH$_2$Ph), 1.55 (2H, CH$_2$CH$_3$), 1.30 (m, 2H, CH$_2$CH$_3$), 0.85 (t, 3H, J 7.5 Hz, CH$_2$CH$_3$), 0.72 (t, 3H, J 7.5 Hz, CH$_2$CH$_3$).

The following aldehydes were also prepared using a similar procedure:

2-Ethylpiperidinyl-2-(2-[2-phenylethoxy]-5-formyl)phenoxy-2-phenylacetamide

N-Ethyl-N-cyclohexyl-2-(2-[2-phenylethoxy]-5-formyl)phenoxy-2-phenylacetamide

4-Phenylpiperazinyl-2-(2-[2-phenylethoxy]-5-formyl)phenoxy-2-phenylacetamide

N-Ethyl-N-iso-propyl-2-(2-[2-phenylethoxy]-5-formyl)phenoxy-2-phenylacetamide

Example 24

3-[[(Methylsulfonyl)oxy]methyl]-4-(phenylmethoxy)benzaldehyde

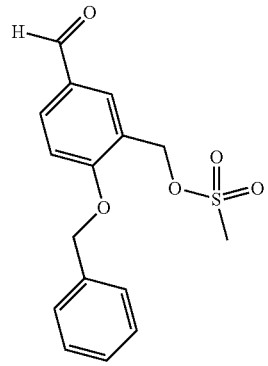

Methanesulfonyl chloride (2.50 g) was added to a stirred solution of 3-(hydroxymethyl)-4-phenylmethoxybenzaldehyde (4.00 g) in dichloromethane (50 ml) at 0° C. To this solution was then added diisopropylethylamine (8.1 ml) over approx. 2 minutes. After stirring for a further 5 minutes the reaction mixture was partitioned between dichloromethane and water. The organic layer was washed with dilute hydrochloric acid, dried over sodium sulfate, filtered and concentrated under reduced pressure to give pale straw coloured oil. Addition of diethyl ether caused the product to crystallize. This material was collected and washed with more diethyl ether to give 3-[[(methylsulfonyl)oxy]methyl]-4-phenylmethoxybenzaldehyde (4.51 g) as off-white crystals. $^1$H NMR (CDCl$_3$) δ 9.78 (s, 1H, CHO); 5.22 (s, 2H); 5.10 (s, 2H); 2.83 (s, 3H). TLC (silica gel): R$_f$=0.4 (dichloromethane:diethyl ether, 24:1).

Example 25

3-[[(Methylsulfonyl)oxy]methyl]-4-(2-phenylethoxy)benzaldehyde

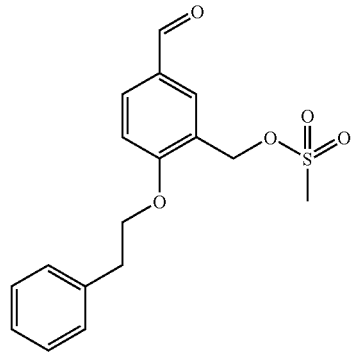

This compound was prepared from 3-(hydroxymethyl)-4-(2-phenylethoxy)benzaldehyde (1.05 g, 1 eq) using the same procedure as that described in Example 10, except that the product was not crystalline. Instead, it was purified by chromatography on silica gel and elution with dichloromethane:diethyl ether (5:1) gave the product as a colourless gum (1.40 g, 99%). R$_F$ (petroleum ether:diethyl ether, 1:1) 0.10. $^1$H NMR (CDCl$_3$) δ 9.88 (s, 1H, O=C—H), 7.90 (m, 2H, ArH), 7.03 (d, 1H, J 8.1 Hz, ArH), 5.27 (s, 2H, CH$_2$OSO$_2$CH$_3$), 4.35 (t, 2H, J 6.9 Hz, OCH$_2$CH$_2$Ph), 3.18 (t, 2H, J 6.9 Hz, OCH$_2$CH$_2$Ph), 2.95 (s, 3H, CH$_2$OSO$_2$CH$_3$).

Example 26

3-[(Phenoxy)methyl]-4-phenylmethoxybenzaldehyde

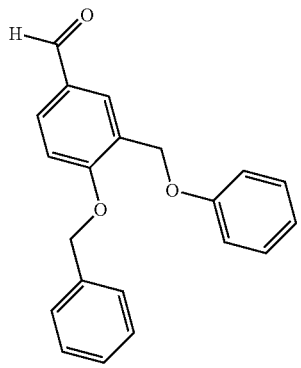

Phenol (100 mg), cesium carbonate (100 mg) and 3-[[(methylsulfonyl)oxy]methyl]-4-phenylmethoxybenzaldehyde (120 mg) were heated in dimethylformamide (1 ml) at approx. 80° C. for about 30 minutes. TLC showed that the reaction was almost complete so the reaction mixture was partitioned between diethyl ether and water. The organic layer was washed with brine, dried over sodium sulfate, filtered and concentrated under reduced pressure to give an oil. The residue was purified via flash column chromatography, using dichloromethane:diethyl ether (10:1) as eluant to give 3-[(phenoxy)methyl]-4-phenylmethoxybenzaldehyde (90 mg) as off-white crystals. $^1$H NMR (CDCl$_3$) δ 9.95 (s, 1H, CHO); 5.27 (s, 2H); 5.24 (s, 2H). TLC (silica gel): R$_f$=0.7 (petroleum ether: diethyl ether, 1:1).

Example 27

3-(Phenoxymethyl)-4-(2-phenylethoxy)benzaldehyde

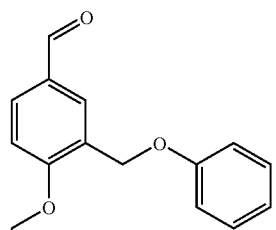

Cesium carbonate (226 mg, 0.69 mmol, 1.5 eq) was added to a stirred solution of 3-[[(methylsulfonyl)oxy]methyl]-4-(2-phenylethoxy)benzaldehyde (155 mg, 0.46 mmol, 1 eq) and phenol (175 mg, 1.86 mmol, 4 eq). The reaction mixture was stirred for 48 h, then partitioned between diethyl ether (50 mL) and water (50 mL). The two layers were separated and the organic layer washed with water (2×100 mL), 1M sodium hydroxide (100 mL), brine (100 mL) and then dried over sodium sulfate and evaporated. The residue was purified by chromatography on silica gel. Elution with dichloromethane gave a gummy solid, which when triturated with ether crystallized to a white powder (105 mg, 68%). R$_F$ (petroleum ether:diethyl ether, 1:1) 0.40. $^1$H NMR (CDCl$_3$) δ 9.90 (s, 1H, O=C—H), 8.04 (s, 1H, ArH), 7.84 (d, 1H, J 8.4 Hz, ArH), 5.08 (s, 2H, CH$_2$OPh), 4.34 (t, 2H, J 6.5 Hz, OCH$_2$CH$_2$Ph), 3.16 (t, 2H, J 6.5 Hz, OCH$_2$CH$_2$Ph).

Example 28

3-(Phenylmethoxy)-4-(2-[4-chlorophenyl]ethoxy)benzaldehyde

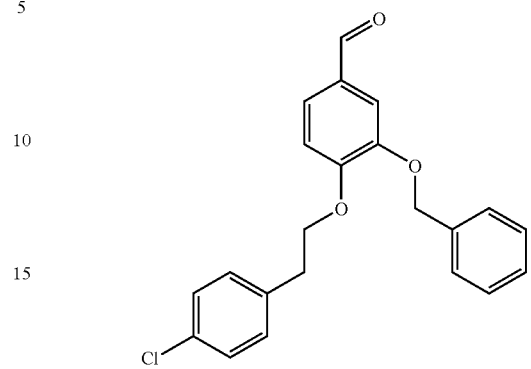

Methane 2-(4-chlorophenyl)ethyl sulfonate (467 mg, 1.97 mmol, 1.5 eq) was added to a stirred solution of 4-hydroxy-3-(phenylmethoxy)benzaldehyde (300 mg, 1.31 mmol, 1 eq) and cesium carbonate (450 mg, 1.38 mmol, 1 eq) in N,N-dimethylformamide (10 mL). The reaction mixture was heated to 70° C. and stirred for 4 h. It was then concentrated in vacuo, and the residue diluted with ethyl acetate (100 mL). The organic solution was washed with 1M HCl (2×100 mL), 2M sodium hydroxide (100 mL), 1M HCl (100 mL), brine (100 mL) and then dried over sodium sulfate and evaporated. This gave a brown gum, which was recrystallized from ethyl acetate and petroleum ether to give a pale brown powder (260 mg, 54%). R$_F$ (dichloromethane) 0.69. $^1$H NMR (CDCl$_3$) δ9.83 (s, 1H, O=C—H), 6.96 (d, 1H, J 8.1 Hz, ArH), 5.14 (s, 2H, OCH$_2$Ph), 4.28 (t, 2H, J 6.6 Hz, OCH$_2$CH$_2$Ph), 3.14 (t, 2H, J 6.6 Hz, OCH$_2$CH$_2$Ph).

The following compounds were prepared using a similar procedure:

3-(Phenylmethoxy)-4-(2-[4-fluorophenyl]ethoxy)benzaldehyde 3-(Phenylmethoxy)-4-[(S)-2-phenylpropoxy]benzaldehyde

Example 29

5-[[3,4-bis(phenylmethoxy)phenyl]methylene]-4-oxo-2-thioxo-3-thiazolidineacetic acid

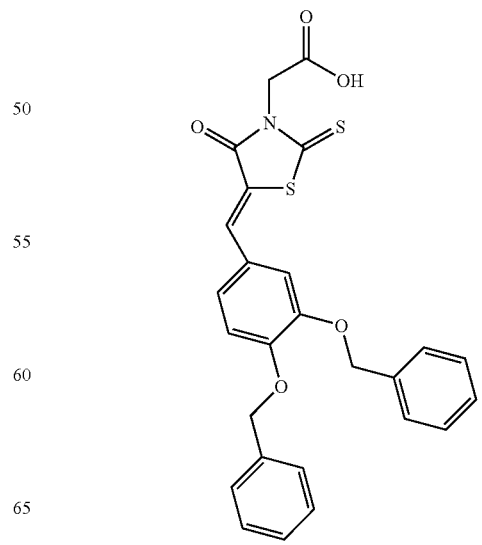

A solution of rhodanine-3-acetic acid (1 g, 5.20 mmol, 1 eq), 3,4-dibenzyloxybenzaldehyde (2.04 g, 6.25 mmol, 1.2 eq), and sodium acetate (1.3 g, 15.6 mmol, 3 eq) in acetic acid (30 ml) was heated to reflux, and stirred overnight. As the reaction mixture cooled to room temperature the product precipitated and it was filtered and washed with acetic acid, then petroleum ether. The gummy solid was dissolved in ethyl acetate (20 mL) and extracted into saturated aqueous sodium bicarbonate (2×30 mL). The basic extracts were combined, washed with ethyl acetate, and acidified to pH 1 with concentrated HCl. The aqueous solution was extracted with ethyl acetate (2×10 mL), and the organic extracts combined, dried over sodium sulfate and evaporated in vacuo. Recrystallization from ethyl acetate and petroleum ether gave the product which was suspended in water and freeze-dried overnight in vacuo to give the product as a fluffy yellow powder (2.1 g, 81%). mp 235–238° C.: $^1$H NMR (d6 DMSO) δ 7.79 (s, 1H, C═C—H), 5.25 (s, 2H, CH$_2$Ph), 5.23 (s, 2H, CH$_2$Ph), 4.73 (s, 2H, C$\underline{H}_2$CO$_2$H). Anal. Found: C, 63.53; H, 4.31; N, 2.85; S, 13.05. Calcd for C$_{26}$H$_{21}$NO$_5$S$_2$: C, 63.39; H, 4.21; N, 2.84; S, 12.92.

Example 30

5-[[4-Methoxy-3-(phenylmethoxy)phenyl]methylene]-4-oxo-2-thioxo-3-thiazolidineacetic acid

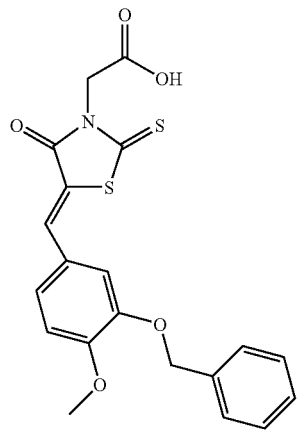

This compound was prepared from 3-benzyloxy-4-methoxybenzaldehyde (355 mg, 1.2 eq) using the same procedure as for Example 29. The product precipitated from the reaction mixture, so was washed with acetic acid and petroleum ether, then suspended in water and freeze-dried overnight in vacuo to give the product as a yellow powder (405 mg, 97%) mp 234–239° C.: $^1$H NMR (d6 DMSO) δ 7.81 (s, 1H, C═C—H), 5.18 (s, 2H, CH$_2$Ph), 4.73 (s, 2H, C$\underline{H}_2$HCO$_2$H), 3.86 (s, 3H, CH$_3$).

Example 31

5-[[3,4,5-Tris(phenylmethoxy)phenyl]methylene]-4-oxo-2-thioxo-3-thiazolidineacetic acid

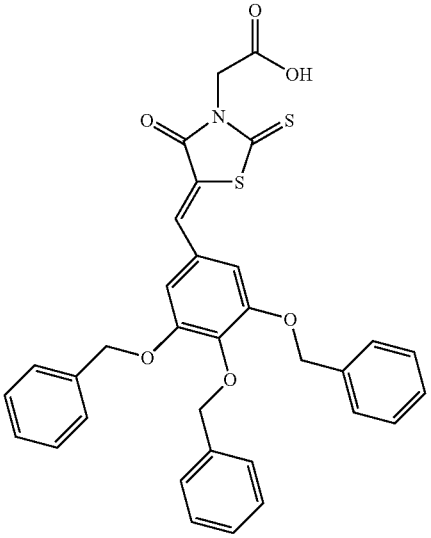

This compound was prepared from 3,4,5-tribenzyloxybenzaldehyde (278 mg, 1.2 eq) using the same procedure as for Example 30 and was obtained as a yellow powder (256 mg, 80%) mp 213–216° C.: $^1$H NMR (d6 DMSO) δ 7.72 (s, 1H, C═C—H), 5.22 (s, 4H, 2×CH$_2$Ph), 5.05 (s, 2H, CH$_2$Ph), 4.50 (s, 2H, C$\underline{H}_2$CO$_2$H).

Example 32

5-[[3,4-Bis[(4-fluorophenyl)methoxy]phenyl]methylene]-4-oxo-2-thioxo-3-thiazolidineacetic acid

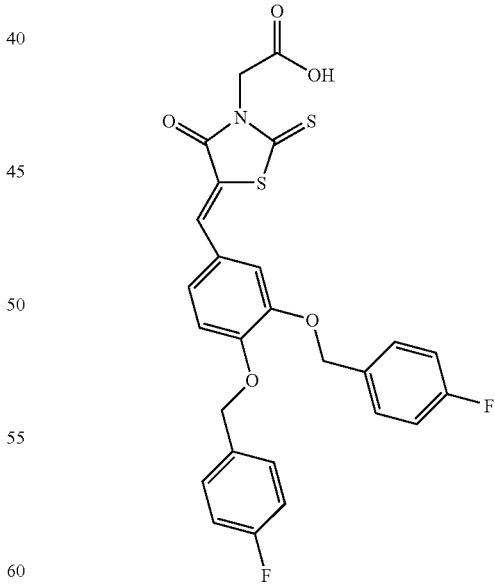

This compound was prepared from 3,4-bis[(4-fluorophenyl)methoxy]benzaldehyde (445 mg, 1.2 eq) using the same procedure as for Example 30 and was obtained as a yellow powder (367 mg, 67%) mp 229° C. (dec): $^1$H NMR (d6 DMSO) δ 7.75 (s, 1H, C═C—H), 5.20 (s, 2H, CH$_2$Ar), 5.19 (s, 2H, CH$_2$Ar), 4.54 (s, 2H, C$\underline{H}_2$CO$_2$H).

Example 33

5-[[3,4-Bis[(4-methoxyphenyl)methoxy]phenyl]methylene]-4-oxo-2-thioxo-3-thiazolidineacetic acid

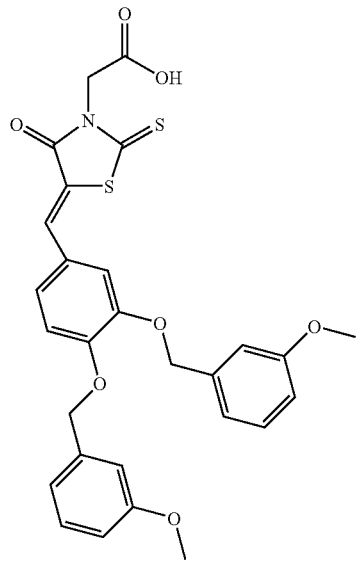

This compound was prepared from 3,4-bis[(3-methoxyphenyl)methoxy]benzaldehyde (475 mg, 1.2 eq) using the same procedure as for Example 30 and was obtained as a yellow powder (312 mg, 54%) mp 151–155° C.: $^1$H NMR (d6 DMSO) δ 7.79 (s, 1H, C=C—H), 5.22 (s, 2H, CH$_2$Ar), 5.21 (s, 2H, CH$_2$Ar), 4.72 (s, 2H, C$\underline{H}_2$CO$_2$H), 3.73 (s, 6H, 2×CH$_3$).

Example 34

5-[[3,4-Bis[(2,4-difluorophenyl)methoxy]phenyl]methylene]-4-oxo-2-thioxo-3-thiazolidineacetic acid

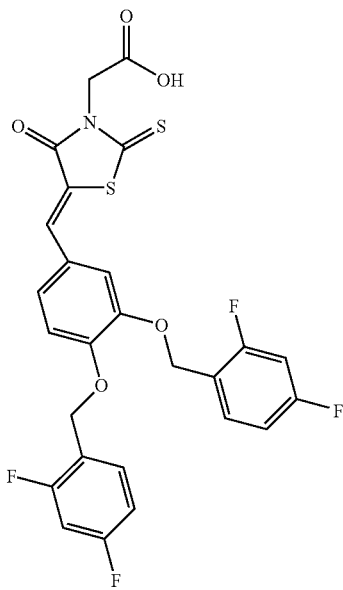

This compound was prepared from 3,4-bis[(2,4-difluorophenyl)methoxy]-benzaldehyde (408 mg, 1 eq) using the same procedure as for Example 29. The product precipitated from the reaction mixture and was washed with acetic acid, water and diethyl ether. This gave a gummy solid which was recrystallized from methanol, acetone and petroleum ether, then suspended in water and freeze-dried overnight in vacuo to give the product as a yellow powder (220 mg, 37%) mp 251–254° C.: $^1$H NMR (d6 DMSO) δ 7.71 (s, 1H, C=C—H), 5.44 (s, 2H, CH$_2$Ar), 5.23 (s, 2H, CH$_2$Ar), 4.26 (s, 2H, C$\underline{H}_2$CO$_2$H).

Example 35

5-[[4-Pentyloxy-3-(phenylmethoxy)phenyl]methylene]-4-oxo-2-thioxo-3-thiazolidineacetic acid

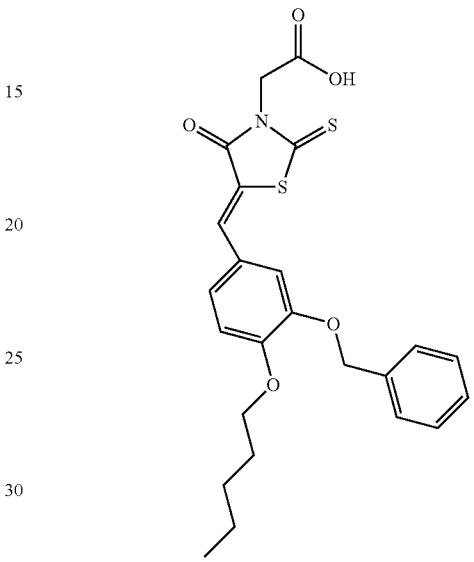

This compound was prepared from 3-benzyloxy-4-n-pentyloxybenzaldehyde (171 mg, 1.15 eq) using the same procedure as for Example 30 and was obtained as a yellow powder (42 mg, 17%) mp 229–234° C.: $^1$H NMR (d6 DMSO) δ 7.73 (s, 1H, C=C—H), 5.20 (s, 2H, CH$_2$Ph), 4.48 (s, 2H, C$\underline{H}_2$CO$_2$H), 4.08 (t, 2H, OCH$_2$), 1.75 (m, 2H, OCH$_2$C$\underline{H}_2$), 1.33 (m, 4H, C$\underline{H}_2$C$\underline{H}_2$CH$_3$), 0.88 (t, 3H, CH$_3$).

Example 36

5-[[3-(Phenylmethoxy)-4-[(2-phenyl)ethoxy]phenyl]methylene]-4-oxo-2-thioxo-3-thiazolidineacetic acid

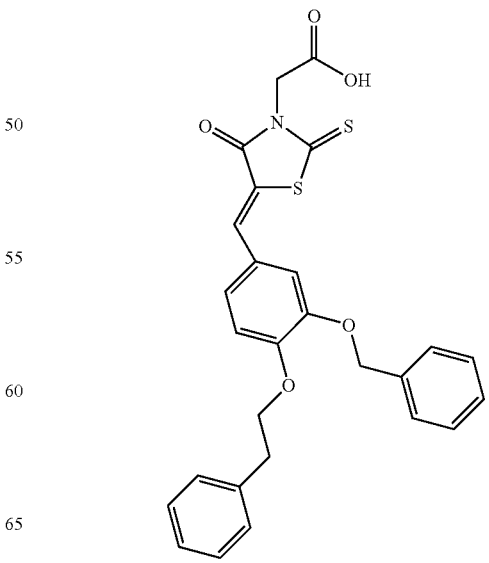

This compound was prepared from 3-benzyloxy-4-(2-phenylethoxy)benzaldehyde (261 mg, 1 eq) using the same procedure as for Example 29. A gummy solid precipitated from the reaction mixture which was dissolved in ethyl acetate (20 mL) and washed with 10% HCl (aq) (2×20 mL), then water (2×20 mL). The organic solution was dried over sodium sulfate and evaporated in vacuo. Recrystallization from acetone and petroleum ether gave the product which was suspended in water and freeze-dried overnight in vacuo to give the product as a yellow powder (188 mg, 47%) mp 198–201° C.: $^1$H NMR (d6 DMSO) δ 7.80 (s, 1H, C═C—H), 5.17 (s, 2H, CH$_2$Ph), 4.71 (s, 2H, CH$_2$CO$_2$H), 4.31 (t, 2H, CH$_2$CH$_2$Ph), 3.07 (t, 2H, CH$_2$CH$_2$Ph).

Example 37

5-[[4-[(3,4-Difluorophenyl)methoxy]-3-(Phenylmethoxy)phenyl]-methylene]-4-oxo-2-thioxo-3-thiazolidineacetic acid

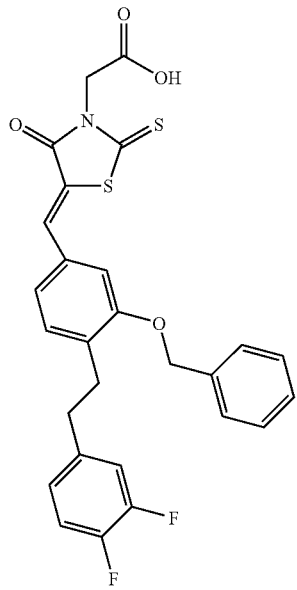

This compound was prepared from 3-benzyloxy-4-(3,4-difluorophenyl)methoxybenzaldehyde (185 mg, 1 eq) using the same procedure as for Example 29. The product precipitated from the reaction mixture and was washed sequentially with acetic acid, water, diethyl ether and petroleum ether. It was then suspended in water and freeze-dried overnight in vacuo to give the product as a yellow powder (221 mg, 80%) mp 236° C. (dec): $^1$H NMR (d6 DMSO) δ 7.71 (s, 1H, C═C—H), 5.22 (s, 2H, CH$_2$Ar), 5.21 (s, 2H, CH$_2$Ar), 4.42 (s, 2H, CH$_2$CO$_2$H).

Example 38

5-[[4-[(4-Trifluoromethylphenyl)methoxy]-3-(phenylmethoxy)phenyl]methylene]-4-oxo-2-thioxo-3-thiazolidineacetic acid

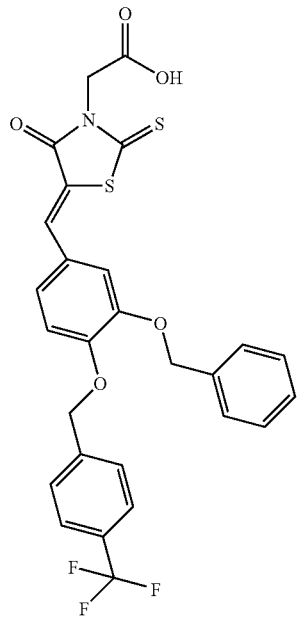

This compound was prepared from 3-(phenylmethoxy)-4-[(4-trifluoromethylphenyl)methoxy]benzaldehyde (300 mg, 1 eq) using the same procedure as for Example 29. A gummy solid precipitated from the reaction mixture which was recrystallized from methanol:ethyl acetate (1:2) and petroleum ether and freeze-dried overnight in vacuo to give the product as a yellow powder (177 mg, 40%) mp 257–263° C.: $^1$H NMR (d6 DMSO) δ 7.74 (s, 1H, C═C—H), 5.37 (s, 2H, CH$_2$Ar), 5.25 (s, 2H, CH$_2$Ph), 4.47 (s, 2H, CH$_2$CO$_2$H).

Example 39

5-[[3-(Phenylmethoxy)-4-[(3-trifluoromethylphenyl)methoxy]phenyl]-methylene]-4-oxo-2-thioxo-3-thiazolidineacetic acid

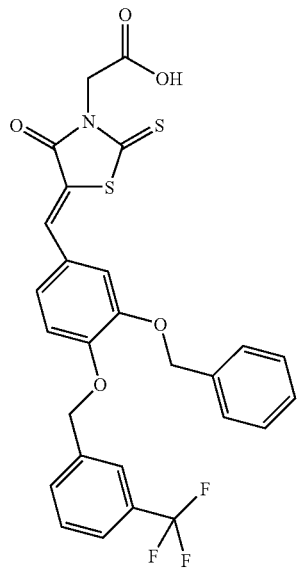

This compound was prepared from 3-phenylmethoxy-4-[(3-trifluoromethylphenyl)methoxy]benzaldehyde (300 mg, 1 eq) using the same procedure as for Example 29. A gummy solid precipitated from the reaction mixture which was dissolved in ethyl acetate (20 mL) and washed with 10% HCl (aq) (2×20 mL), then water (2×20 mL). The organic solution was dried over sodium sulfate and evaporated in vacuo. Recrystallization from ethyl acetate and petroleum ether gave the product, which was suspended in water and freeze-dried overnight in vacuo to give a yellow powder, (211 mg, 48%) mp 187–194° C.: $^1$H NMR (d6 DMSO) δ 7.82 (s, 1H, C=C—H), 5.36 (s, 2H, CH$_2$Ar), 5.24 (s, 2H, CH$_2$Ph), 4.73 (s, 2H, C$\underline{H}_2$CO$_2$H).

Example 40

5-[[4-[(2,4-Difluorophenyl)methoxy]-3-(phenylmethoxy)phenyl]-methylene]-4-oxo-2-thioxo-3-thiazolidineacetic acid

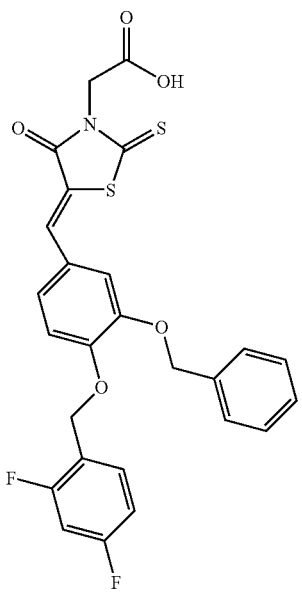

This compound was prepared from 4-(2,4-difluorophenyl)methoxy-3-(phenylmethoxy)benzaldehyde (278 mg, 1 eq) using the same procedure as for Example 37 and was obtained as a yellow powder (112 mg, 27%) mp 236–239° C.: $^1$H NMR (d6 DMSO) δ 7.75 (s, 1H, C=C—H), 5.24 (s, 2H, CH$_2$Ar), 5.21 (s, 2H, CH$_2$Ph), 4.51 (s, 2H, C$\underline{H}_2$CO$_2$H).

Example 41

5-[[4-[(4-Methylsulfonylphenyl)methoxy]-3-(phenylmethoxy)phenyl]-methylene]-4-oxo-2-thioxo-3-thiazolidineacetic acid

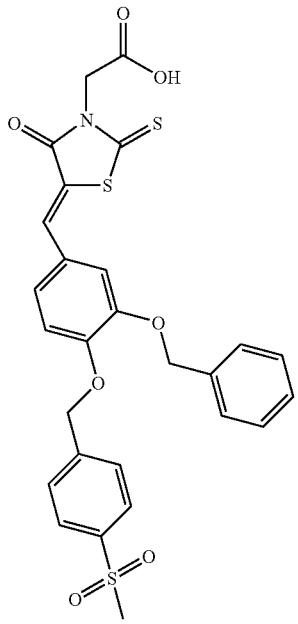

This compound was prepared from 4-(4-methylsulfonylphenyl)methoxy-3-(phenylmethoxy)benzaldehyde (311 mg, 1 eq) using the same procedure as for Example 37 and was obtained as a yellow powder (164 mg, 37%). $^1$H NMR (d6 DMSO) δ 7.72 (s, 1H, C=C—H), 5.38 (s, 2H, CH$_2$Ar), 5.24 (s, 2H, CH$_2$Ph), 4.49 (s, 2H, C$\underline{H}_2$CO$_2$H), 3.22 (s, 3H, CH$_3$).

Example 42

5-[[3-(Phenylmethoxy)-4-[(4-trifluoromethoxyphenyl)methoxy]-phenyl]-methylene]-4-oxo-2-thioxo-3-thiazolidineacetic acid

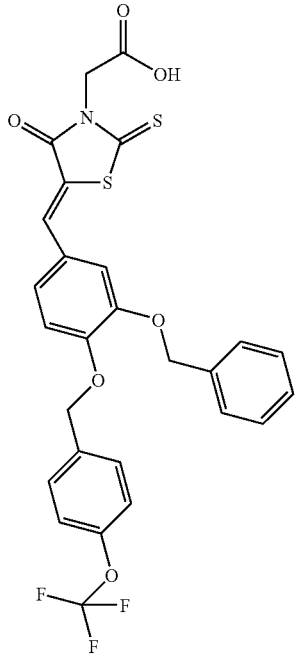

This compound was prepared from 3-(phenylmethoxy)-4-[(4-trifluoromethoxyphenyl)methoxy]benzaldehyde (210 mg, 1 eq) using the same procedure as for Example 37 and was obtained as a yellow/orange powder (121 mg, 40%) mp 195–199° C.: $^1$H NMR (d6 DMSO) δ 7.79 (s, 1H, C═C—H), 5.29 (s, 2H, CH$_2$Ar), 5.24 (s, 2H, CH$_2$Ph), 4.69 (s, 2H, CH$_2$CO$_2$H).

Example 43

5-[[3-(Phenylmethoxy)-4-[(4-methylphenyl)methoxy]phenyl]-methylene]-4-oxo-2-thioxo-3-thiazolidineacetic acid

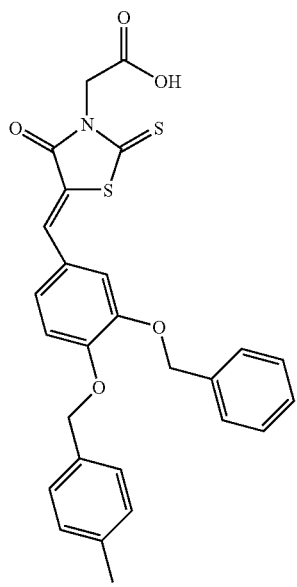

This compound was prepared from 4-(4-methylphenyl-methoxy)-3-(phenylmethoxy)benzaldehyde (330 mg, 1 eq) using the same procedure as for Example 37 and was obtained as a yellow powder (269 mg, 54%) mp 229° C. (dec): $^1$H NMR (d6 DMSO) δ 7.70 (s, 1H, C═C—H), 5.20 (s, 2H, CH$_2$Ar), 5.18 (s, 2H, CH$_2$Ar), 4.43 (s, 2H, CH$_2$CO$_2$H), 2.31 (s, 3H, CH$_3$).

Example 44

5-[[4-[(4-Chlorophenyl)methoxy] 3-(phenylmethoxy)phenyl]-methylene]-4-oxo-2-thioxo-3-thiazolidineacetic acid

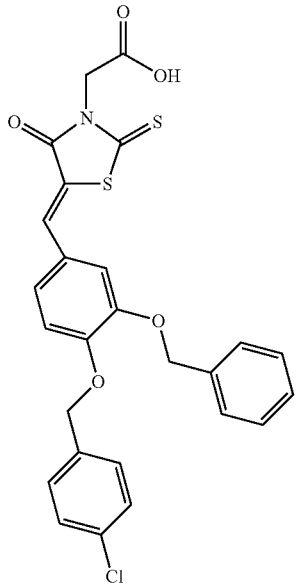

This compound was prepared from 4-(4-chlorophenyl-methoxy)-3-(phenylmethoxy)benzaldehyde (150 mg, 1 eq) using the same procedure as for Example 37 and was obtained as a yellow powder (93 mg, 42%) mp 244° C. (dec): $^1$H NMR (d6 DMSO) δ 7.73 (s, 1H, C═C—H), 5.24 (s, 2H, CH$_2$Ar), 5.23 (s, 2H, CH$_2$Ar), 4.49 (s, 2H, CH$_2$CO$_2$H).

Example 45

5-[[3-(Phenylmethoxy)-4-(2-pyridylmethoxy)phenyl]methylene]-4-oxo-2-thioxo-3-thiazolidineacetic acid

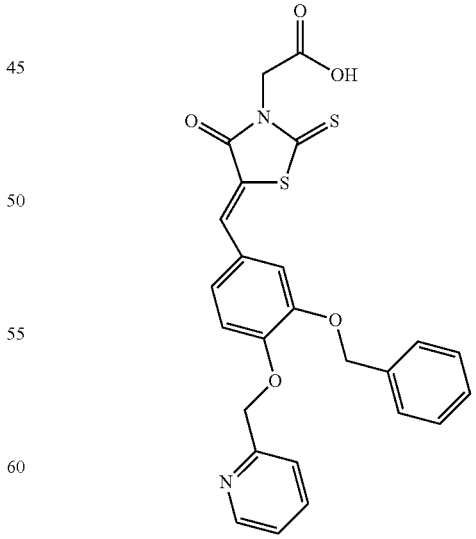

This compound was prepared from 3-(phenylmethoxy)-4-(2-pyridylmethoxy)benzaldehyde (140 mg, 1 eq) using the same procedure as for Example 37 and was obtained as a yellow powder (87 mg, 40%) mp 238° C. (dec): $^1$H NMR (d6 DMSO) δ 8.59 (m, 1H, pyH), 7.83 (m, 1H, pyH), 7.81 (s, 1H, C=C—H), 5.33 (s, 2H, CH₂Ar), 5.26 (s, 2H, CH₂Ph), 4.72 (s, 2H, C$\underline{H}$₂CO₂H).

Example 46

5-[[4-[[3,5-bis(trifluoromethyl)phenyl]methoxy]-3-(Phenylmethoxy)phenyl]methylene]-4-oxo-2-thioxo-3-thiazolidineacetic acid

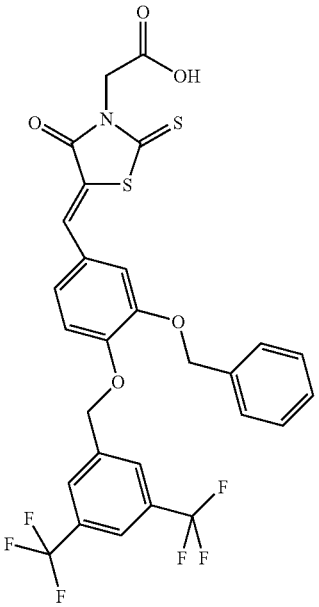

This compound was prepared from 4-[(3,5-bis(trifluoromethyl)phenyl]methoxy-3-(phenylmethoxy)benzaldehyde (238 mg, 1 eq) using the same procedure as for Example 37 and was obtained as a yellow powder (124 mg, 43%) mp 221° C. (dec): ¹H NMR (d6 DMSO) δ 7.72 (s, 1H, C=C—H), 5.43 (s, 2H, CH₂Ar), 5.23 (s, 2H, CH₂Ph), 4.48 (s, 2H, C$\underline{H}$₂CO₂H).

Example 47

5-[[4-(Phenylmethoxy)-3-(2-pyridylmethoxy)phenyl]methylene]-4-oxo-2-thioxo-3-thiazolidineacetic acid

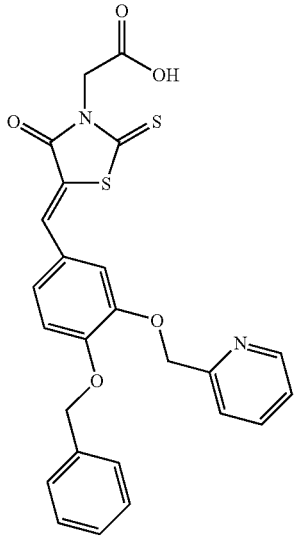

This compound was prepared from 4-(phenylmethoxy)-3-(2-pyridylmethoxy)benzaldehyde (408 mg, 1.2 eq) using the same procedure as for Example 37 and was obtained as a yellow powder (411 mg, 80%) mp 204–207° C.: ¹H NMR (d6 DMSO) δ 8.59 (m, 1H, pyH), 7.82 (m, 1H, pyH), 7.77 (s, 1H, C=C—H), 5.31 (s, 2H, CH₂Ar), 5.26 (s, 2H, CH₂Ph), 4.67 (s, 2H, C$\underline{H}$₂CO₂H).

Example 48

5-[[3-[(alpha-Methoxycarbonyl)phenylmethoxy]-4-(phenylmethoxy)phenyl]methylene]-4-oxo-2-thioxo-3-thiazolidineacetic acid

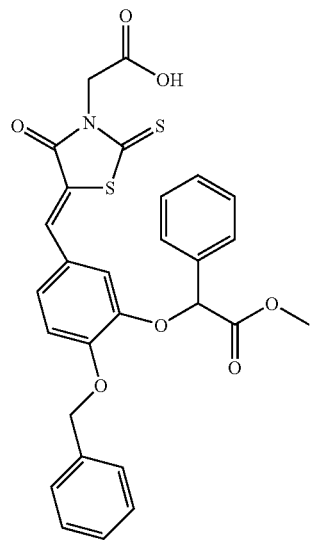

This compound was prepared from methyl 2-(2-phenylmethoxy-5-formyl)phenoxy-2-phenylacetate (471 mg, 1.2 eq) using the same procedure as for Example 29. The product did not precipitate readily from the reaction mixture, so it was concentrated in vacuo and diluted with ethyl acetate (20 mL). The organic solution was extracted with saturated aqueous sodium bicarbonate (3×20 mL) and the basic extracts combined, then washed with ethyl acetate (20 mL). The aqueous solution was acidified to pH 1 with 10% HCl and back extracted with ethyl acetate (2×20 mL). The organic extracts were combined, dried over sodium sulfate, and evaporated in vacuo, and the residue chromatographed on silica with ethyl acetate:petroleum ether:acetic acid (79:19:2). The product was recrystallized from acetone and petroleum ether, suspended in water, and freeze-dried overnight to give a yellow powder (112 mg, 20%) mp 140–142° C.: ¹H NMR (d6 DMSO) δ 7.80 (s, 1H, C=C—H), 6.07 (s, 1H, CHPh), 5.28 (s, 2H, CH₂Ph), 4.73 (s, 2H, C$\underline{H}$₂CO₂H), 3.70 (s, 3H, CH₃).

Example 49

5-[[3-[(3,4-difluorophenyl)methoxy]-4-(phenyl-methoxy)phenyl]-methylene]-4-oxo-2-thioxo-3-thiazolidineacetic acid

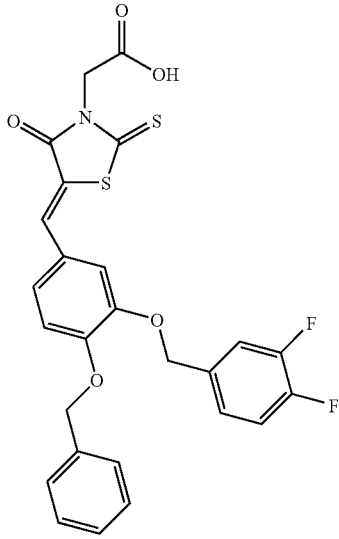

This compound was prepared from 3-(3,4-difluorophenyl)methoxy-4-phenylmethoxybenzaldehyde (213 mg, 1.2 eq) using the same procedure as for Example 37 and was obtained as a yellow solid (107 mg, 39%) mp 231–236° C.: $^1$H NMR (CDCl$_3$) δ 7.72 (s, 1H, C=C—H), 5.23 (s, 2H, CH$_2$Ar), 5.20 (s, 2H, CH$_2$Ar), 4.43 (s, 2H, CH$_2$CO$_2$H).

Example 50

5-[[3-[(4-Methylsulfonylphenyl)methoxy]-4-(phenylmethoxy)phenyl]methylene]-4-oxo-2-thioxo-3-thiazolidineacetic acid

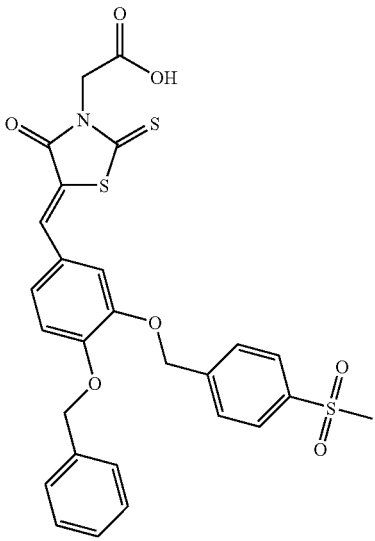

This compound was prepared from 3-[(4-methylsulfonylphenyl)methoxy]-4-(phenylmethoxy)benzaldehyde (250 mg, 1 eq) using the same procedure as for Example 37 and was obtained as a yellow solid (134 mg, 37%) mp 207–211° C.: $^1$H NMR (d6 DMSO) δ 7.76 (s, 1H, C=C—H), 5.37 (s, 2H, CH$_2$Ar), 5.26 (s, 2H, CH$_2$Ph), 4.60 (s, 2H, CH$_2$CO$_2$H), 3.22 (s, 3H, CH$_3$).

Example 51

5-[[3-(Phenylmethoxy)-4-[2-(4-chlorophenyl)ethoxy]phenyl]-methylene]-4-oxo-2-thioxo-3-thiazolidineacetic acid

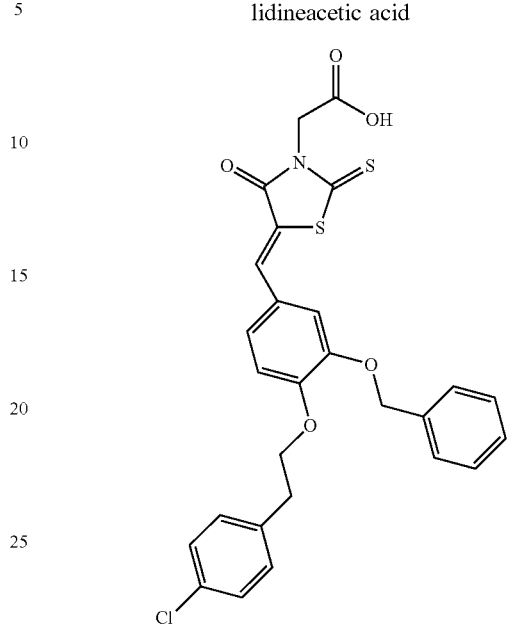

This compound was prepared from 3-(phenylmethoxy)-4-(2-[4-chlorophenyl]ethoxy)benzaldehyde (260 mg, 1 eq) using the same procedure as that described in Example 36, except that the product was recrystallized from ethyl acetate (190 mg, 50%) mp 202° C.: $^1$H NMR (d6 DMSO) δ7.80 (s, 1H, C=C—H) 5.15 (s, 2H, OCH$_2$Ph), 4.72 (s, 2H, CH$_2$CO$_2$H), 4.29 (t, 2H, J 6.4 Hz, OCH$_2$CH$_2$Ph), 3.06 (t, 2H, J 6.4 Hz, OCH$_2$CH$_2$Ph).

Example 52

5-[[3-(Phenylmethoxy)-4-[2-(4-fluorophenyl)ethoxy]phenyl]methylene]-4-oxo-2-thioxo-3-thiazolidineacetic acid

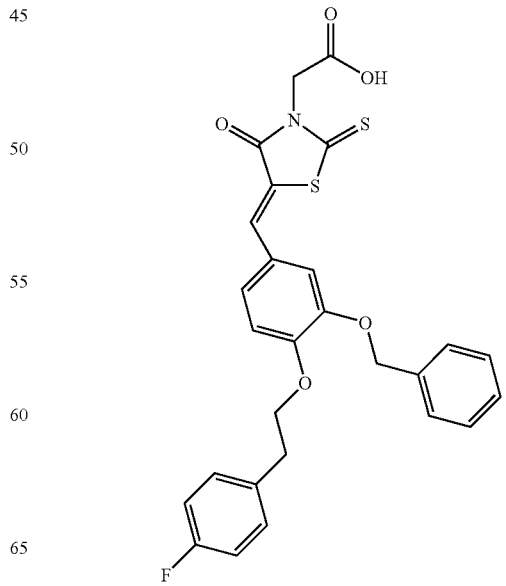

This compound was prepared from 3-(phenylmethoxy)-4-(2-[4-fluorophenyl]ethoxy)benzaldehyde (366 mg, 1 eq) using the same procedure as that described in Example 51 and was obtained as a yellow powder (266 mg, 49%) mp 221° C.: ¹H NMR (d6 DMSO) δ7.79 (s, 1H, C=C—H) 5.15 (s, 2H, OCH₂Ph), 4.71 (s, 2H, CH₂CO₂H), 4.28 (m, 2H, OCH₂CH₂Ph), 3.06 (m, 2H, OCH₂CH₂Ph).

Example 53

5-[[3-(Phenylmethoxy)-4-[(S)-2-phenylpropyloxy]phenyl]methylene]-4-oxo-2-thioxo-3-thiazolidineacetic acid

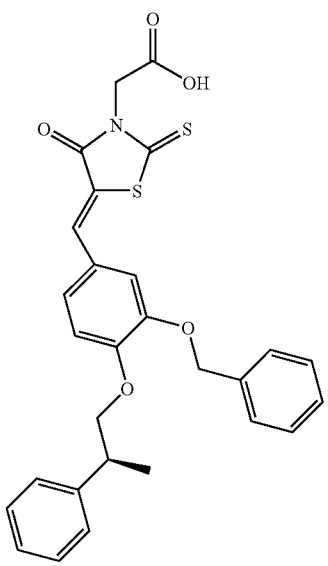

This compound was prepared from 3-(phenylmethoxy)-4-[(S)-2-phenylpropoxy]-benzaldehyde (280 mg, 1 eq) using the same procedure as in Example 76, except that the reaction required 5 h, and was obtained as a yellow powder (75 mg, 18%) mp 148° C.: ¹H NMR (d6 DMSO) δ7.80 (s, 1H, C=C—H) 5.14 (s, 2H, OCH₂Ph), 4.72 (s, 2H, CH₂CO₂H), 4.19 (m, 2H, OCH₂CHCH₃Ph), 3.27 (m, 1H, OCH₂CHCH₃Ph), 1.34 (d, 3H, J 6.8 Hz, OCH₂CHCH₃Ph).

Example 54

5-[[3-(Phenylmethoxy)-4-[2-cyclohexylethoxy]phenyl]methylene]-4-oxo-2-thioxo-3-thiazolidineacetic acid

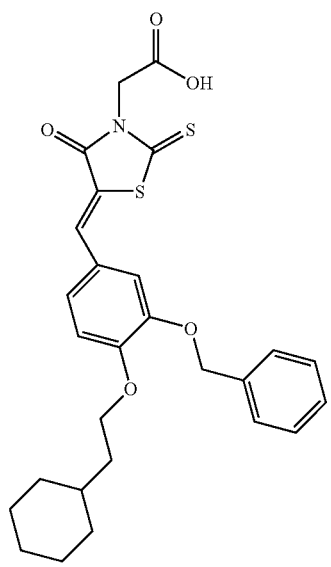

This compound was prepared from 3-(phenylmethoxy)-4-(2-cyclohexylethoxy)benzaldehyde (283 mg, 1 eq) using the same procedure as outlined in Example 78, except that the product was recrystallized from ethyl acetate and diethyl ether (247 mg, 58%) mp 218° C.: ¹H NMR (d6 DMSO) δ7.80 (s, 1H, C=C—H) 5.20 (s, 2H, OCH₂Ph), 4.73 (s, 2H, CH₂CO₂H), 4.13 (t, 2H, J 6.4 Hz, OCH₂ CH₂).

Example 55

5-[[3-(2-Pyridylmethoxy)-4-(2-phenylethoxy)phenyl]methylene]-4-oxo-2-thioxo-3-thiazolidineacetic acid hydrochloride salt

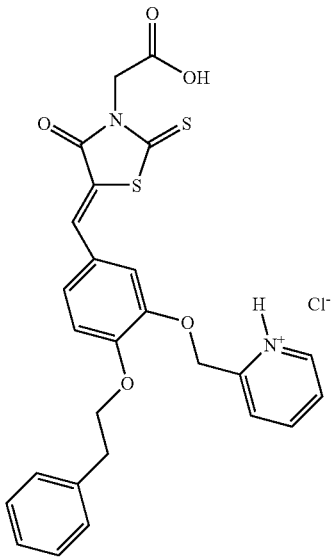

A solution of 3-[(2-pyridyl)methoxy]-4-(2-phenylethoxy)benzaldehyde (367 mg, 1.101 mmol, 1 eq) rhodanine-3-acetic acid (210 mg, 1.101 mmol, 1 eq), and ammonium acetate (424 mg, 5.5 mmol, 5 eq) in toluene (10 mL) was heated to 110° C. and stirred for 6.5 h. The reaction mixture was cooled to room temperature and dissolved in a mixture of ethyl acetate, 1M HCl and acetic acid (one-phase). This was filtered and concentrated in vacuo. The residue was recrystallized from acetic acid and water to give a yellow powder, which was washed with water and diethyl ether, then suspended in water and freeze-dried overnight (236 mg, 42%) mp 190° C.: $^1$H NMR (d6 DMSO) $\delta$8.75 (d, 1H, J 4.5 Hz, pyH), 8.19 (dd, 1H, J 7.2 and 7.2 Hz, pyH), 7.83 (s, 1H, C=C—H), 5.37 (s, 2H, OCH$_2$py), 4.73 (s, 2H, CH$_2$CO$_2$H), 4.34 (t, 2H, J 6.0 Hz, OC$\underline{H}_2$CH$_2$Ph), 3.08 (t, 2H, J 6.4 Hz, OCH$_2$C$\underline{H}_2$Ph).

Example 56

5-[[3-(1-Phenyl-2,2,2-trifluoroethoxy)-4-[2-phenylethoxy]phenyl]methylene]-4-oxo-2-thioxo-3-thiazolidineacetic acid

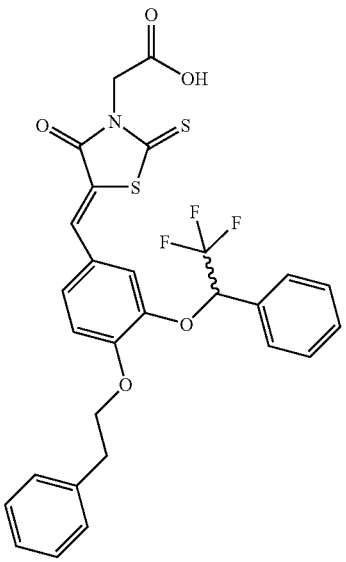

A solution of rhodanine-3-acetic acid (87 mg, 0.46 mmol, 1 eq), 3-(1-phenyl-2,2,2-trifluoroethoxy)-4-(2-phenylethoxy)benzaldehyde (183 mg, 0.46 mmol, 1 eq) and sodium acetate (112 mg, 1.37 mmol, 3 eq) in acetic acid (2 mL) was heated to 150□C and stirred for 3.5 days. The reaction mixture was then cooled to room temperature and partitioned between ethyl acetate (50 mL) and water (50 mL) and the two layers separated. The organic layer was washed with 1M HCl (2×50 mL), and loaded onto silica. Elution with ethyl acetate:methanol (4:1) gave a yellow gum. This was dissolved in hot ethyl acetate and filtered (to remove some insoluble material). The filtrate was allowed to cool to room temperature and diethyl ether added. This gave a suspension which was again filtered. The filtrate was evaporated and the residue redissolved in diethyl ether. Addition of petroleum ether to the solution gave a precipitate which was filtered off. The mother liquor was evaporated and the resulting gum was crystallized from diethyl ether and petroleum ether to give the product as a yellow powder (107 mg, 41%) mp 170° C.: $^1$H NMR (d6 DMSO) $\delta$ 7.67 (s, 1H, C=C—H), 6.17 (q, 1H, J 6.5 Hz, CHCF$_3$), 4.70 (s, 2H, CH$_2$CO$_2$H), 4.33 (t, 2H, J 5.9 Hz, OC$\underline{H}_2$CH$_2$Ph), 3.09 (t, 2H, J 6.2 Hz, OCH$_2$C$\underline{H}_2$Ph).

Example 57

5-[[3-[(R)-1-Phenyl-2,2,2-trifluoroethoxy]-4-[2-phenylethoxy]phenyl]methylene]-4-oxo-2-thioxo-3-thiazolidineacetic acid

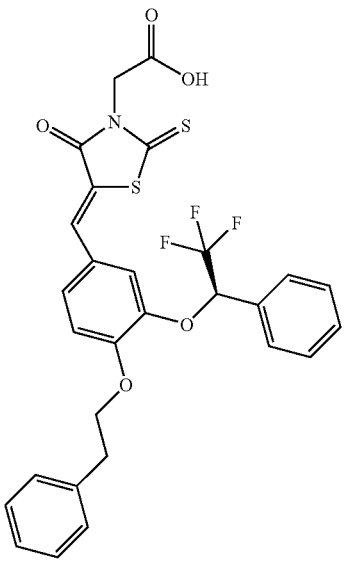

This compound was prepared from 3-[(R)-1-phenyl-2,2,2-trifluoroethoxy]-4-(2-phenylethoxy)benzaldehyde (120 mg, 1 eq) using the procedure described in Example 78 (105 mg, 61%) mp 167° C.: $^1$H NMR (d6 DMSO) $\delta$ 7.67 (s, 1H, C=C—H), 6.17 (q, 1H, J 6.4 Hz, CHCF$_3$), 4.70 (s, 2H, CH$_2$CO$_2$H), 4.33 (t, 2H, J 6.0 Hz, OC$\underline{H}_2$CH$_2$Ph), 3.09 (t, 2H, J 6.0 Hz, OCH$_2$C$\underline{H}_2$Ph).

Example 58

5-[[3-[(S)-1-Phenyl-2,2,2-trifluoroethoxy]-4-[2-phenylethoxy]phenyl]methylene]-4-oxo-2-thioxo-3-thiazolidineacetic acid

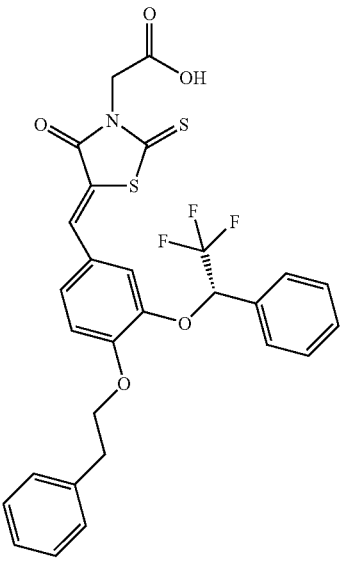

This compound was prepared from 3-[(S)-1-phenyl-2,2,2-trifluoroethoxy]-4-(2-phenylethoxy)benzaldehyde (90 mg, 1 eq) using the procedure described in Example 78, except that the product was purified by chromatography on silica gel. Elution with ethyl acetate:methanol (9:1) gave a gummy solid which was dissolved in ethyl acetate and filtered. The filtrate was evaporated, and the residue recrystallized from diethyl ether and petroleum ether to give the product as a yellow powder (25 mg, 20%) mp 168° C.: $^1$H NMR (d6 DMSO) δ 7.67 (s, 1H, C=C—H), 6.17 (q, 1H, J 6.4 Hz, CHCF$_3$), 4.70 (s, 2H, CH$_2$CO$_2$H), 4.33 (t, 2H, J 6.0 Hz, OCH$_2$CH$_2$Ph), 3.09 (t, 2H, J 6.0 Hz, OCH$_2$CH$_2$Ph).

Example 59

5-[[3-[(S)-1-Phenyl-2,2,2-trifluoroethoxy]-4-[(R)-2-phenylpropoxy]phenyl]-methylene]-4-oxo-2-thioxo-3-thiazolidineacetic acid

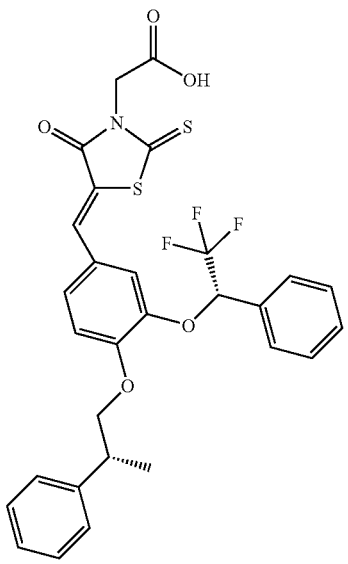

This compound was prepared from 3-[(S)-1-phenyl-2,2,2-trifluoroethoxy]-4-[(R)-2-phenylpropoxy]benzaldehyde (120 mg, 1 eq) using the procedure as described in Example 78, except that the reaction required 1.5 h. The product was recrystallized from diethyl ether (63 mg, 37%) mp 184° C.: $^1$H NMR (d6 DMSO) δ 7.67 (s, 1H, C=C—H), 6.16 (q, 1H, J 6.4 Hz, CHCF$_3$), 4.70 (s, 2H, CH$_2$CO$_2$H), 4.20 (d, 2H, J 6.4 Hz, OCH$_2$CHCH$_3$Ph), 3.23 (m, 1H, OCH$_2$CHCH$_3$Ph), 1.34 (d, 3H, J 6.8 Hz, OCH$_2$CHCH$_3$Ph) $^{19}$F NMR (d6 DMSO) −75.83.

Example 60

5-[[3-[(S)-1-Phenyl-2,2,2-trifluoroethoxy]-4-[(S)-2-phenylpropoxy]-phenyl]methylene]-4-oxo-2-thioxo-3-thiazolidineacetic acid

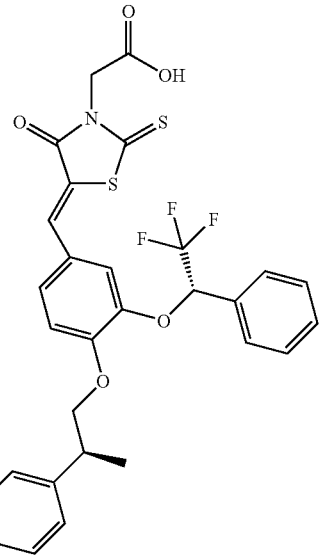

A solution of rhodanine-3-acetic acid (461 mg, 2.41 mmol, 1 eq), 3-[(S)-1-phenyl-2,2,2-trifluoroethoxy]-4-[(S)-2-phenylpropoxy]benzaldehyde (1.0 g, 2.41 mmol, 1 eq) and ammonium acetate (558 mg, 7.24 mmol, 3 eq) in N,N-dimethylformamide (10 mL) was heated to 90° C. and stirred for 15 min. It was then cooled to room temperature and diluted with ethyl acetate (100 mL). The organic solution was washed with 1M HCl (2×200 mL), and brine (200 mL), then dried over sodium sulfate and evaporated. The residue was purified by chromatography on silica gel; elution with ethyl acetate followed by ethyl acetate:methanol (9:1) gave a yellow gum which was dissolved in methanol (5 mL) and added dropwise to stirred ice-cold water (100 mL). A fine suspension was obtained, which was freeze-dried over 3 days to give the product as a yellow powder (1.04 g, 73%) mp 73–80° C.: $^1$H NMR (d6 DMSO) δ 7.64 (s, 1H, C=C—H), 6.04 (q, 1H, J 6.4 Hz, CHCF$_3$), 4.61 (s, 2H, CH$_2$CO$_2$H), 4.22 (m, 2H, OCH$_2$CHCH$_3$Ph), 3.26 (m, 1H, OCH$_2$CHCH$_3$Ph), 1.38 (d, 3H, J 7.2 Hz, OCH$_2$CHCH$_3$Ph) $^{19}$F NMR (d6 DMSO) −75.80. Anal. Found: C, 59.31; H, 4.42; N, 2.36; Calcd for C$_{29}$H$_{24}$F$_3$NO$_5$S$_2$: C, 59.27; H, 4.12; N, 2.38.

Example 61

5-[[3-(Phenylmethoxy)-4-(2,2,3,3,3-pentafluoropropoxy)phenyl]methylene]-4-oxo-2-thioxo-3-thiazolidineacetic acid

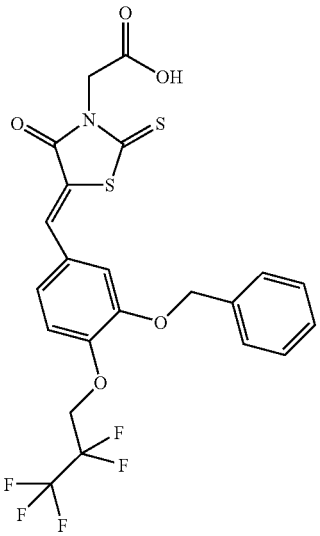

This compound was prepared from 3-(phenylmethoxy)-4-(2,2,3,3,3-pentafluoropropoxy)benzaldehyde (300 mg, 1 eq) using the procedure described in Example 78 (280 mg, 63%) mp 171° C.: $^1$H NMR (d6 DMSO) δ 7.83 (s, 1H, C=C—H), 5.24 (s, 2H, OCH$_2$Ph), 4.96 (t, 2H, J 12.8 Hz, OCH$_2$CF$_2$), 4.74 (s, 2H, CH$_2$CO$_2$H), $^{19}$F NMR (d6 DMSO) −82.87, −122.74.

Example 62

5-[[3-(1-Phenylethoxy)-4-(2-phenylethoxy)]phenyl]methylene]-4-oxo-2-thioxo-3-thiazolidineacetic acid

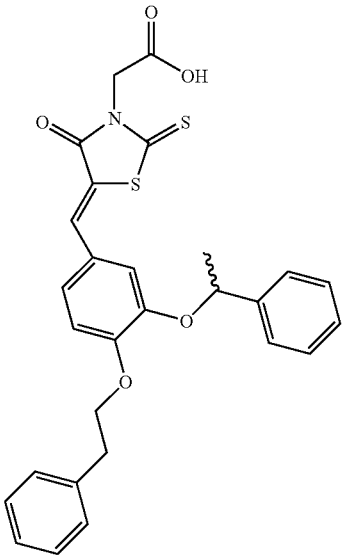

This compound was prepared from 3-(1-phenylethoxy)-4-(2-phenylethoxy)benzaldehyde (680 mg, 1 eq) using the procedure described in Example 60, except that the reaction was heated to 70° C. and was complete in 10 min. The product was recrystallized from ethyl acetate/diethyl ether/petroleum ether and was obtained as a yellow powder (763 mg, 75%) mp 166° C.: $^1$H NMR (d6 DMSO) δ7.69 (s, 1H, C=C—H), 7.02 (d, 1H, J 1.9 Hz, ArH), 5.44 (q, 1H, J 6.4 Hz, OCHCH$_3$Ph), 4.70 (s, 2H, CH$_2$CO$_2$H), 4.32 (t, 2H, J 6.4 Hz, OCH$_2$CH$_2$Ph), 3.11 (t, 2H, J 6.4 Hz, OCH$_2$CH$_2$Ph), 1.55 (d, 3H, J 6.4 Hz, OCHCH$_3$Ph).

Example 63

5-[[3-(1-Phenyl-2-hydroxy)ethoxy)-4-(2-phenylethoxy)]phenyl]methylene]-4-oxo-2-thioxo-3-thiazolidineacetic acid

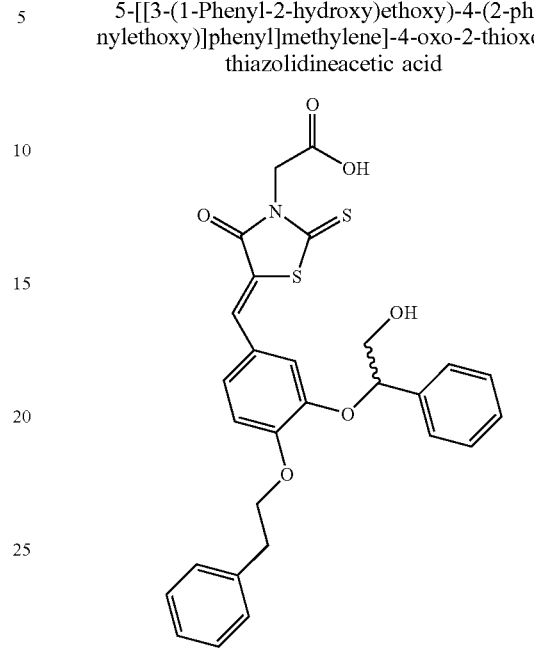

This compound was prepared from 3-[(1-phenyl-2-hydroxy)ethoxy]-4-(2-phenylethoxy)-benzaldehyde (300 mg, 0.828 mmol, 1 eq) using the procedure described in Example 78. After work-up the residue was purified by chromatography on silica gel. Elution with ethyl acetate gave a yellow gum, which was recrystallized from diethyl ether and petroleum ether to give the product as a yellow powder (147 mg, 33%) mp 133° C.: $^1$H NMR (d6 DMSO) δ 7.70 (s, 1H, C=C—H), 5.35 (m, 1H, OCHPh), 5.08 (s, 1H, OH), 4.70 (s, 2H, CH$_2$CO$_2$H), 4.32 (m, 2H, OCH$_2$CH$_2$Ph), 3.80 (m, 1H, CH$_2$OH), 3.64 (m, 1H, CH$_2$OH), 3.10 (t, 2H, J 6.0 Hz, OCH$_2$CH$_2$Ph).

Example 64

5-[[4-(Phenylmethoxy)-3-[(alpha-di-n-propylaminocarbonyl)phenylmethoxy]phenyl]methylene]-4-oxo-2-thioxo-3-thiazolidineacetic acid

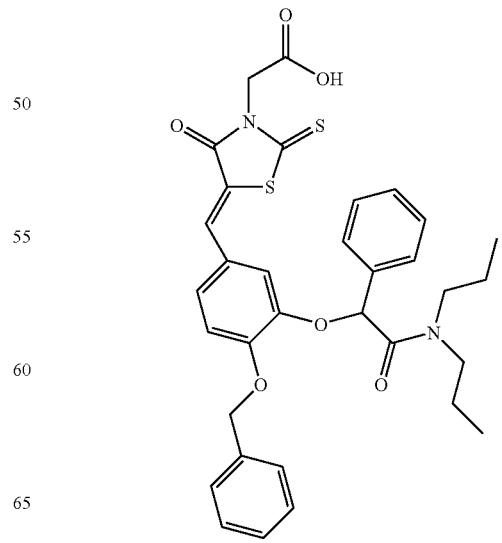

This compound was prepared from N,N-di-n-propyl-2-(2-phenylmethoxy-5-formyl)phenoxy-2-phenylacetamide (349 mg, 1 eq) using the same procedure as for Example 29. The reaction mixture was concentrated in vacuo and the residue dissolved in ethyl acetate (20 mL) and washed with 10% HCl (aq) (2×20 mL), then water (2×20 mL), then brine (20 mL). The organic solution was dried over sodium sulfate and evaporated in vacuo. This gave a gummy solid, which was recrystallized from dichloromethane and petroleum ether. The product was suspended in water and freeze-dried overnight in vacuo to give the product as a yellow powder (250 mg, 52%) mp 194–197° C.: $^1$H NMR (d6 DMSO) δ 7.74 (s, 1H, C=C—H), 6.24 (s, 1H, CHPh), 5.26 (s, 2H, CH$_2$Ph), 4.73 (s, 2H, C$\underline{H}_2$CO$_2$H).

Example 65

5-[[4-(Phenylmethoxy)-3-[(alpha-2-(phenylethyl)aminocarbonyl)phenylmethoxy]phenyl]methylene]-4-oxo-2-thioxo-3-thiazolidineacetic acid

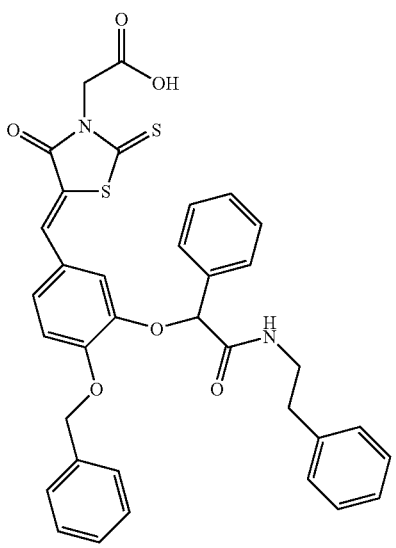

This compound was prepared from N-(2-phenyl)ethyl-2-(2-phenylmethoxy-5-formyl)phenoxy-2-phenylacetamide (365 mg, 1 eq) using the same procedure as for Example 37 and was obtained yellow powder (220 mg, 40%) mp 219–225° C.: $^1$H NMR (d6 DMSO) δ 8.46 (t, 1H, NH), 7.70 (s, 1H, C=C—H), 5.67 (s, 1H, CHPh), 5.26 (s, 2H, CH$_2$Ph), 4.60 (s, 2H, C$\underline{H}_{CO2}$H).

Example 66

5-[[4-(Phenylmethoxy)-3-[(α-(N-benzylaminocarbonyl)phenylmethoxy]phenyl]-methylene]-4-oxo-2-thioxo-3-thiazolidineacetic acid

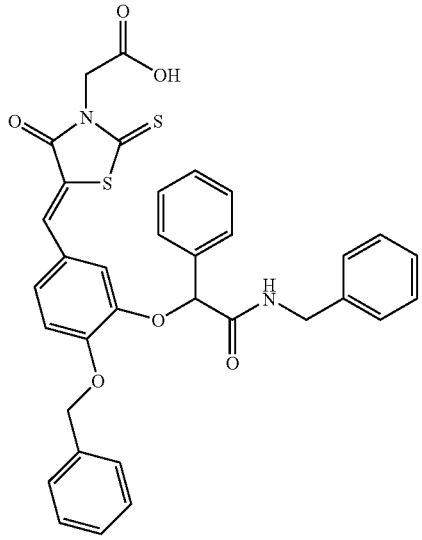

This compound was prepared from N-benzyl-2-(2-phenylmethoxy-5-formyl)phenoxy-2-phenylacetamide (354 mg, 1 eq) using the same procedure as example 64. The product was recrystallized from ethyl acetate and petroleum ether to give the product as a yellow powder (221 mg, 45%) mp 179–186° C.: $^1$H NMR (d6 DMSO) δ 8.97 (t, 1H, J 5.9 Hz, NH), 7.71 (s, 1H, C=C—H), 5.78 (s, 1H, OCHPh), 5.28 (s, 2H, OCH$_2$Ph), 4.74 (s, 2H, CH$_2$CO$_2$H), 4.31 (d, 2H, J 5.9 Hz, NCH$_2$Ph).

Example 67

5-[[4-(Phenylmethoxy)-3-[(α-N-phenylaminocarbonyl)phenylmethoxy]phenyl]-methylene]-4-oxo-2-thioxo-3-thiazolidineacetic acid

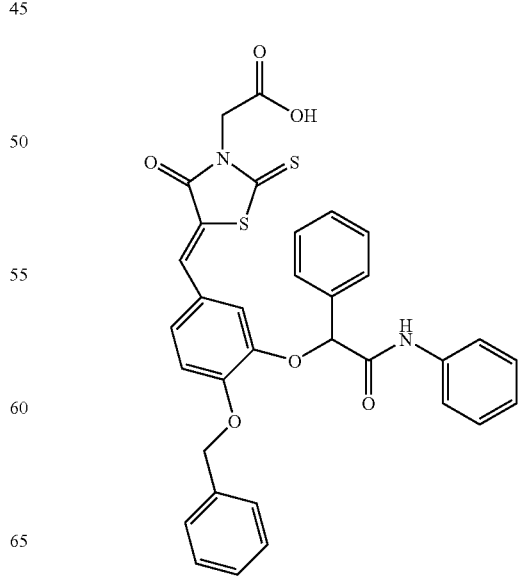

This compound was prepared from N-phenyl-2-(2-phenylmethoxy-5-formyl)phenoxy-2-phenylacetamide (343 mg, 1 eq), using the same procedure as for Example 37 and was obtained as a mustard yellow powder (120 mg, 25%) mp 205–213° C.: $^1$H NMR (d6 DMSO) $\delta$10.59 (s, 1H, NH), 7.68 (s, 1H, C═C—H), 5.94 (s, 1H, OCHPh), 5.30 (s, 2H, OCH$_2$Ph), 4.53 (s, 2H, CH$_2$CO$_2$H).

Example 68

5-[[4-(Phenylmethoxy)-3-[(α-2-ethylpiperidinyl-N-carbonyl)phenylmethoxy]phenyl]-methylene]-4-oxo-2-thioxo-3-thiazolidineacetic acid

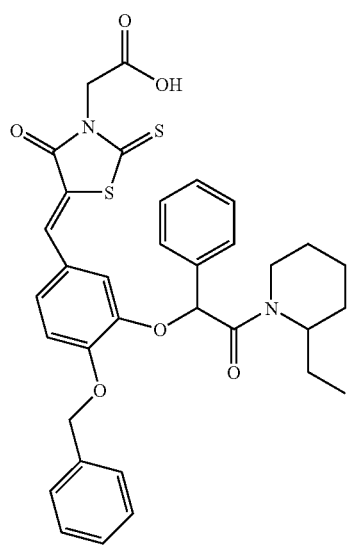

This compound was prepared from 2-ethylpiperidinyl-2-(2-phenylmethoxy-5-formyl)phenoxy-2-phenylacetamide (470 mg, 1 eq) using the same procedure as that described in Example 82, but the product did not require chromatographic purification and was instead crystallized from ethyl acetate and petroleum ether to give the product as a yellow powder (85 mg, 13%) mp 180° C.: $^1$H NMR (d6 DMSO, diastereoisomers/rotamers) $\delta$7.75, 7.74 and 7.71(3×s, 1H, C═C—H), 6.39, 6.31 and 6.24 (3×s, 1H, OCHPh), 5.26 (s, 2H, OCH$_2$Ph), 4.72 (s, 2H, CH$_2$CO$_2$H), 4.49 (m, 1H, NCH$_2$), 4.30 (m, 1H, NCH), 3.89 (m, 1H, NCH$_2$).

Example 69

5-[[4-(Phenylmethoxy)-3-[(α-N-propylaminocarbonyl)phenylmethoxy]-phenyl]methylene]-4-oxo-2-thioxo-3-thiazolidineacetic acid

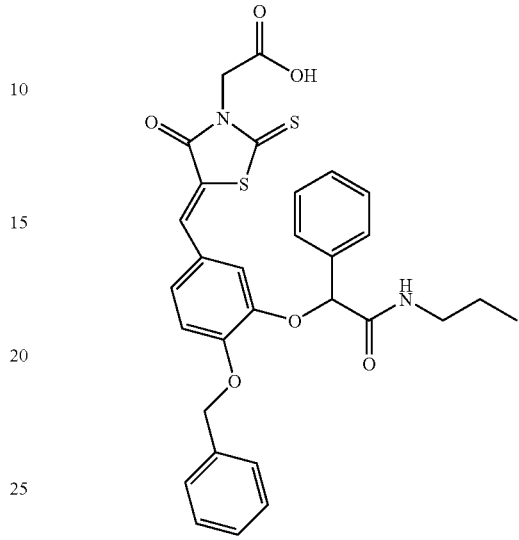

This compound was prepared from N-propyl-2-(2-phenylmethoxy-5-formyl)phenoxy-2-phenylacetamide (140 mg, 1 eq) using the same procedure as that in Example 80 except the product was recrystallized from ethyl acetate as a yellow powder (100 mg, 54%) mp 210–213° C.: $^1$H NMR (d6 DMSO) $\delta$8.38 (s, 1H, NH), 7.74 (s, 1H, C═C—H), 5.68 (s, 1H, OCHPh), 5.28 (s, 2H, OCH$_2$Ph), 4.72 (s, 2H, CH$_2$CO$_2$H), 3.05 (m, 2H, NCH$_2$), 1.38 (m, 2H, CH$_2$CH$_3$), 0.75 (m, 3H, CH$_2$CH$_3$).

Example 70

5-[[4-(Phenylmethoxy)-3-[(α-cis-2,6-dimethylmorpholinyl-N-carbonyl)phenylmethoxy]phenyl]methylene]-4-oxo-2-thioxo-3-thiazolidineacetic acid

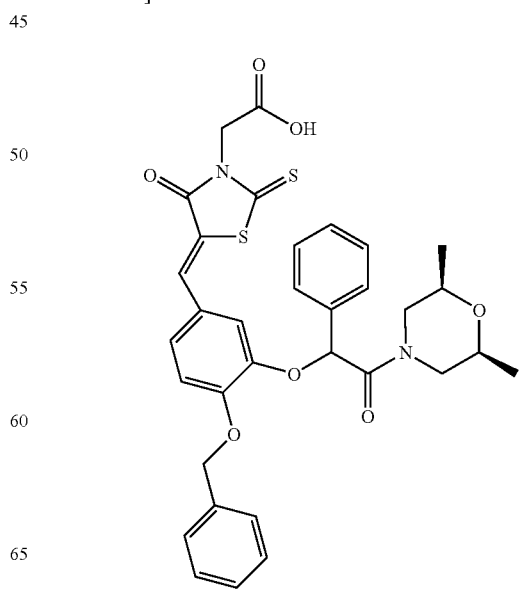

This compound was prepared from cis-2,6-dimethylmorpholinyl-2-(2-phenylmethoxy-5-formyl)phenoxy-2-phenylacetamide (360 mg, 1 eq) using the same procedure as that described in Example 69 and was obtained as a yellow powder (286 mg, 58%) mp 189° C.: $^1$H NMR (d6 DMSO, rotamers) δ7.79 and 7.77 (2×s, 1H, C=C—H), 6.44 and 6.36 (2×s, 1H, OCHPh), 5.27 (s, 2H, OCH$_2$Ph), 4.74 (s, 2H, CH$_2$CO$_2$H), 4.27 (m, 1H, NCH$_2$), 4.03 (m, 1H, NCH$_2$).

Example 71

5-[[4-(Phenylmethoxy)-3-[(α-N,N-di-n-butylaminocarbonyl)phenylmethoxy]phenyl]-methylene]-4-oxo-2-thioxo-3-thiazolidineacetic acid

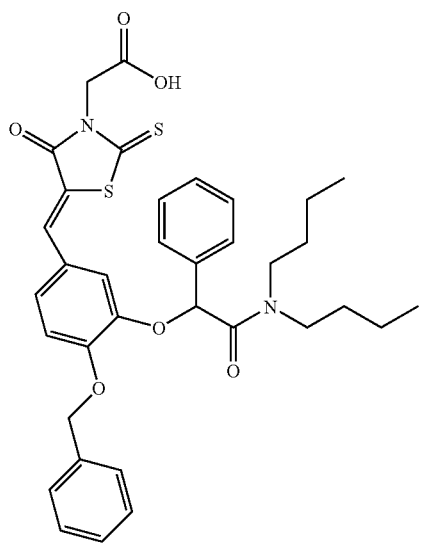

This compound was prepared from N,N-di-butyl-2-(2-phenylmethoxy-5-formyl)phenoxy-2-phenylacetamide (256 mg, 1 eq) using the same procedure as that described in Example 69 and was obtained as a yellow powder (189 mg, 59%) mp 226° C.: $^1$H NMR (d6 DMSO) δ7.75 (s, 1H, C=C—H), 6.25 (s, 1H, OCHPh), 5.26 (s, 2H, OCH$_2$Ph), 4.72 (s, 2H, CH$_2$CO$_2$H), 3.24 (m, 4H, 2×NCH$_2$), 1.38 (m, 4H, 2×NCH$_2$CH$_2$), 1.09 (m, 4H, CH$_2$CH$_3$), 0.78 (t, 3H, J 7.2 Hz, CH$_2$CH$_3$), 0.69 (t, 3H, J 6.9 Hz, CH$_2$CH$_3$).

Example 72

5-[[4-(Phenylmethoxy)-3-[(α-N-n-propyl-N-sec-butylaminocarbonyl)phenylmethoxy]phenyl]methylene]-4-oxo-2-thioxo-3-thiazolidineacetic acid

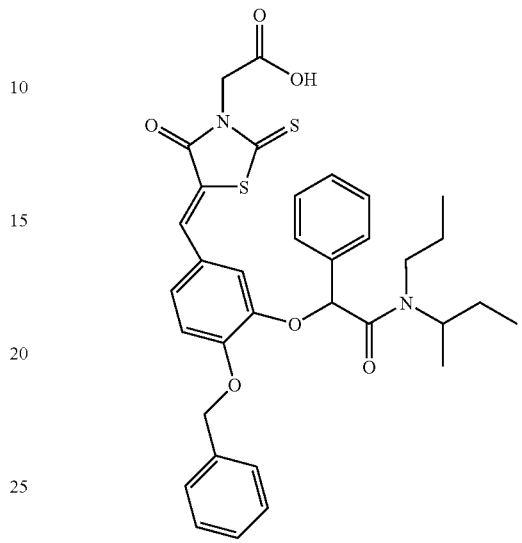

This compound was prepared from N-n-propyl-N-sec-butyl-2-(2-phenylmethoxy-5-formyl)phenoxy-2-phenylacetamide (415 mg, 1 eq) using the procedure described in Example 69 except that the product was crystallized from ethyl acetate and petroleum ether (377 mg, 66%) mp 194° C.: $^1$H NMR (d6 DMSO, rotamers) 7.78 and 7.74 (2×s, 1H, C=C—H), 6.27, 6.23 and 6.12 (3×s, 1H, OCHPh), 5.27 (s, 2H, OCH$_2$Ph), 4.73 (s, 2H, CH$_2$CO$_2$H), 3.88 (m, 1H, NCH$_2$), 3.05 (m, 2H, NCH and NCH$_2$).

Example 73

5-[[4-(Phenylmethoxy)-3-[α-di-n-propylaminocarbonyl)phenylmethoxy]-phenyl]methylene]-2,4-dioxo-3-thiazolidineacetic acid

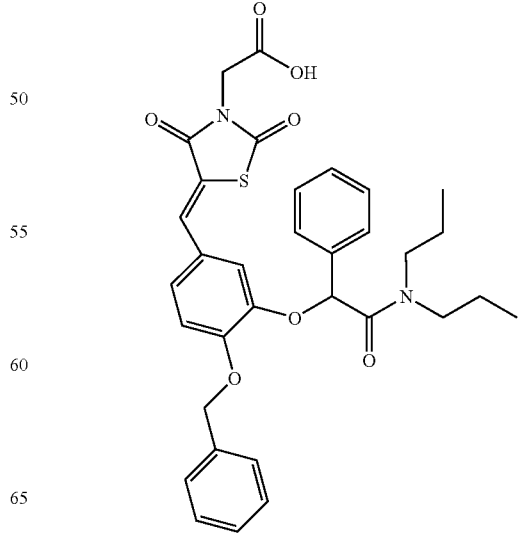

This compound was prepared from 2,4-dioxo-3-thiazolidineacetic acid (100 mg, 1 eq) and N,N-di-n-propyl-2-(2-phenylmethoxy-5-formyl)phenoxy-2-phenylacetamide (260 mg, 1 eq) using the same procedure as that described in Example 36, except that the reaction required 7 days at 150° C. and the product did not crystallize from the reaction mixture. After the work up the crude product was purified by chromatography on silica gel. Elution with ethyl acetate: methanol (9:1) gave the product as a brown gum, which was recrystallized from dichloromethane and ether as a pale brown powder (20 mg, 5%) mp 145° C. (dec.): $^1$H NMR (d6 DMSO) δ 7.75 (s, 1H, C=C—H), 6.19 (s, 1H, OCHPh), 5.25 (2×d, 2H, J 14.6 and 14.6 Hz, OCH$_2$Ph), 3.98 (s, 2H, CH$_2$CO$_2$H), 3.20 (m, 4H, NCH$_2$), 1.40 (m, 4H, CH$_2$CH$_3$), 0.73 (t, 3H, J 7.2 Hz, CH$_2$CH$_3$), 0.62 (t, 3H, J 7.2 Hz, CH$_2$CH$_3$).

Example 74

5-[[4-(2-Phenylethoxy)-3-[α-di-n-propylaminocarbonyl)phenylmethoxy]phenyl]-methylene]-4-oxo-2-thioxo-3-thiazolidineacetic acid

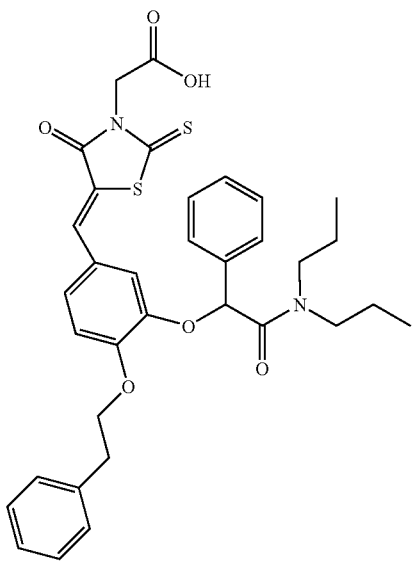

This compound was prepared from N,N-di-n-propyl-2-(2-(2-phenylethoxy)-5-formyl)phenoxy-2-phenylacetamide (400 mg, 1.1 eq) using the same procedure as that described in Example 82, except that the product was eluted with petroleum ether:ethyl acetate (2:1), and recrystallized from ethyl acetate and petroleum ether (70 mg, 13%) mp 79° C.: $^1$H NMR (d6 DMSO) δ 7.75 (s, 1H, C=C—H), 6.20 (s, 1H, OCHPh), 4.73 (s, 2H, CH$_2$CO$_2$H), 4.26 (m, 2H, OCH$_2$CH$_2$Ph), 3.21 (m, 4H, 2×NCH$_2$), 3.03 (t, 2H, J 6.9 Hz, OCH$_2$CH$_2$Ph), 1.40 (m, 4H, 2×CH$_2$CH$_3$), 0.73 (t, 3H, J 7.2 Hz, CH$_2$CH$_3$), 0.63 (t, 3H, J 6.9 Hz, CH$_2$CH$_3$).

Example 75

5-[[4-(2-Phenylethoxy)-3-[(α-2-ethyl-piperidinyl-N-carbonyl)phenylmethoxy]phenyl]-methylene]-4-oxo-2-thioxo-3-thiazolidineacetic acid

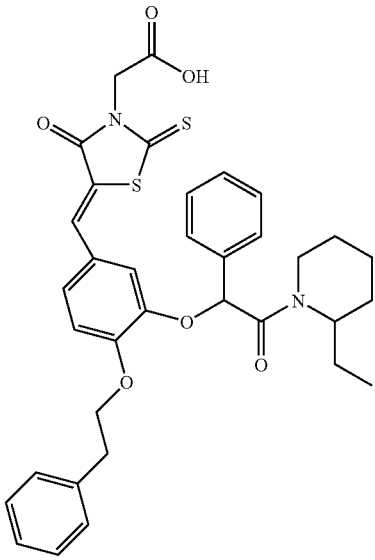

This compound was prepared from 2-ethylpiperidinyl-2-(2-[2-phenylethoxy])-5-formyl)phenoxy-2-phenylacetamide (500 mg, 1 eq) using the procedure described in Example 36, except that it was purified by chromatography on silica gel and elution with petroleum ether:ethyl acetate: acetic acid (33:16:1). A gum was obtained, which was recrystallized from ethyl acetate and petroleum ether to give the product as a yellow powder (83 mg, 12%) mp 202° C.: $^1$H NMR (d6 DMSO, recorded at 80° C. to remove rotamers) δ 7.70 (s, 1H, C=C—H), 6.13 (s, 1H, OCHPh), 4.74 (s, 2H, CH$_2$CO$_2$H), 4.57 (m, 1H, NCH), 4.36 (m, 4H, OCH$_2$CH$_2$Ph and NCH$_2$), 3.07 (m, 2H, OCH$_2$CH$_2$Ph).

Example 76

5-[[4-(2-Phenylethoxy)-3-[α-N-ethyl-N-cyclohexylaminocarbonyl)phenylmethoxy]phenyl]methylene]-4-oxo-2-thioxo-3-thiazolidineacetic acid

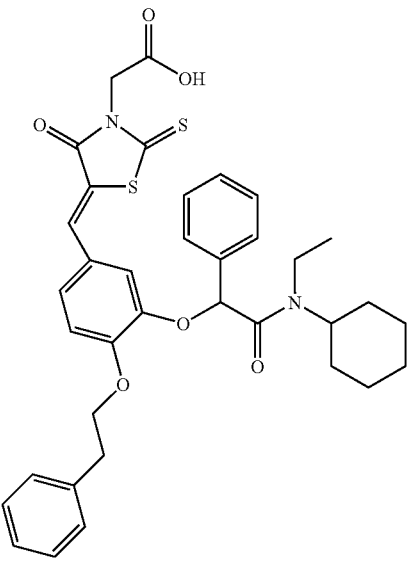

A solution of rhodanine-3-acetic acid (144 mg, 0.75 mmol, 1 eq), N-ethyl-N-cyclohexyl-2-(2-[2-phenylethoxy]-5-formyl)phenoxy-2-phenylacetamide (144 mg, 0.75 mmol, 1 eq) and ammonium acetate (291 mg, 3.77 mmol, 5 eq) in toluene (10 mL) was heated to reflux for 3.5 h. The solution was cooled to room temperature, diluted with ethyl acetate (50 mL) and the organic solution washed with 1M HCl (2×100 mL), followed by brine (100 mL) and dried over sodium sulfate and evaporated. This gave a gummy solid which was crystallized to give the product as a yellow powder using ethyl acetate and petroleum ether (340 mg, 64%) mp 200° C.: $^1$H NMR (d6 DMSO) δ7.75 (s, 1H, C═C—H) 6.29 (s, 1H, OCHPh), 4.76 (s, 2H, CH$_2$CO$_2$H), 4.25 (m, 2H, OCH$_2$CH$_2$Ph), 3.79 (m, 1H, NCH), 3.19 (m, 2H, NCH$_2$), 3.03 (m, 2H, OCH$_2$CH$_2$Ph).

Example 77

5-[[4-(2-Phenylethoxy)-3-[(α-(4-phenylpiperazinyl)-N-carbonyl)phenylmethoxy]-phenyl]methylene]-4-oxo-2-thioxo-3-thiazolidineacetic acid

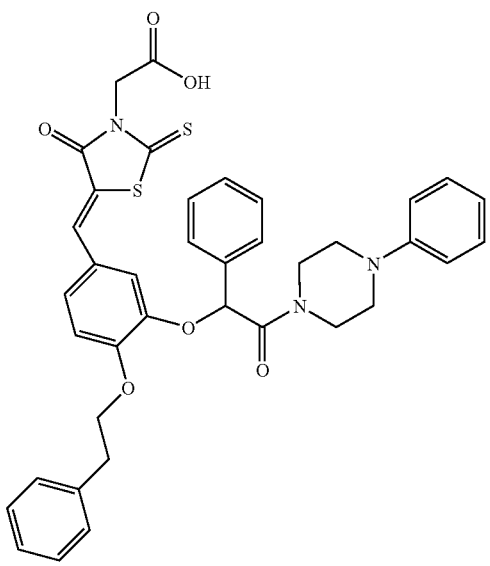

This compound was prepared from 4-phenylpiperazinyl-2-(2-[2-phenylethoxy]-5-formyl)phenoxy-2-phenylacetamide (470 mg, 1 eq) using the procedure outlined in Example 76. After work up the residue was redissolved in minimal ethyl acetate and petroleum ether added dropwise. This gave a gummy brown precipitate, which was collected by filtration. Further addition of petroleum ether to the filtrate gave the product as a bright yellow powder, which was filtered and washed with cold ethyl acetate and petroleum ether (330 mg, 53%) mp 124□C: $^1$H NMR (d6 DMSO) δ7.79 (s, 1H, C═C—H) 6.39 (s, 1H, OCHPh), 4.72 (s, 2H, CH$_2$CO$_2$H), 4.29 (m, 2H, OCH$_2$CH$_2$Ph), 3.62 (m, 4H, 2×NCH$_2$), 3.20 (m, 2H, NCH$_2$), 3.03 (m, 2H, OCH$_2$CH$_2$Ph), 2.88 (m, 2H, NCH$_2$).

Example 78

5-[[4-(2-Phenylethoxy)-3-[(α-N-ethyl-N-iso-propylaminocarbonyl)phenylmethoxy]phenyl]methylene]-4-oxo-2-thioxo-3-thiazolidineacetic acid

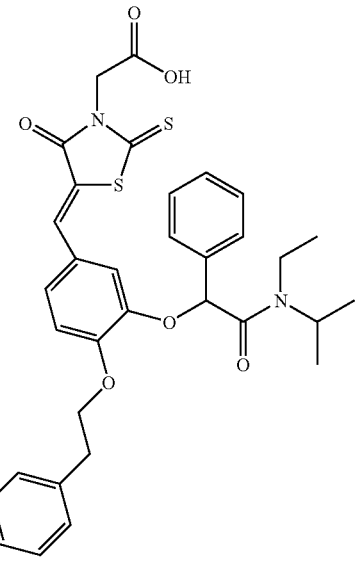

This compound was prepared from N-ethyl-N-iso-propyl-2-(2-[2-phenylethoxy]-5-formyl)phenoxy-2-phenylacetamide (298 mg, 1 eq), and ammonium acetate (155 mg, 3 eq) using the procedure outlined in Example 76 to give the product as a yellow powder (119 mg, 29%) mp 172° C.: $^1$H NMR (d6 DMSO) δ7.75 (s, 1H, C═C—H) 6.26 (s, 1H, OCHPh), 4.73 (s, 2H, CH$_2$CO$_2$H), 4.29 (t, 2H, J 6.8 Hz, OCH$_2$CH$_2$Ph), 4.20 (m, 1H, NCH), 3.15 (m, 2H, NCH$_2$), 3.03 (t, 2H, J 6.4 Hz, OCH$_2$CH$_2$Ph).

Example 79

5-[[4-(2-Phenylethoxy)-3-[(α-N-ethyl-N-cyclohexylcarbonyl)phenylmethoxy]phenyl]-methylene]-2,4-dioxo-3-thiazolidineacetic acid

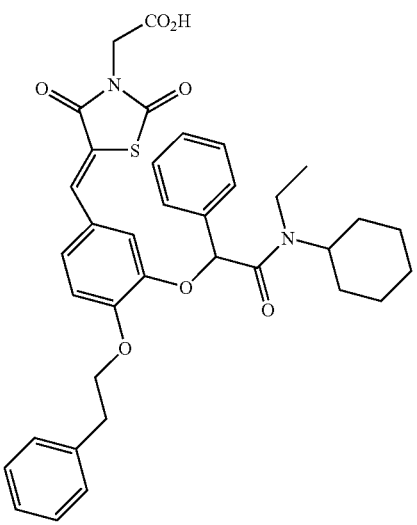

This compound was prepared from 2,4-dioxo-3-thiazolidineacetic acid (108 mg, 1 eq) and 2-ethylpiperidinyl-2-(2-[2-phenylethoxy])-5-formyl)phenoxy-2-phenylacetamide (300 mg, 1 eq) using the same procedure as that used for Example 73, except that the product was eluted with petroleum ether:ethyl acetate:acetic acid (49:49:2), then recrystallized from ethyl acetate and petroleum ether to give a cream coloured powder (12 mg, 3%) mp 75–80° C.: $^1$H NMR (d6 DMSO) δ 7.83 (s, 1H, C=C—H) 6.21 (s, 1H, OCHPh), 4.34 (s, 2H, CH$_2$CO$_2$H), 4.30 (m, 3H, OCH$_2$CH$_2$Ph and NCH$_2$), 3.05 (t, 2H, J 6.4 Hz, OCH$_2$CH$_2$Ph).

Example 80

5-[[3,4-Bis(phenylmethoxy)phenyl]methylene]-2,4-dioxo-3-thiazolidineacetic acid

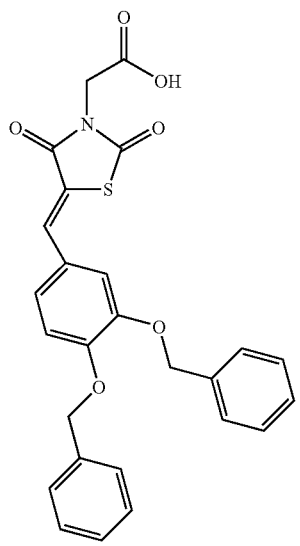

This compound was prepared from 2,4-dioxo-3-thiazolidineacetic acid (182 mg, 1 eq) using the same procedure as for Example 12. The solvent was removed in vacuo and the residue chromatographed on silica with petroleum ether:ethyl acetate:acetic acid (49:49:1) as eluent. The product was suspended in water and freeze-dried overnight in vacuo to give a yellow powder (27 mg, 5%) mp 167–170° C.: $^1$H NMR (CD$_3$OD) δ 7.79 (s, 1H, C=C—H), 5.20 (s, 2H, CH$_2$Ph), 5.18 (s, 2H, CH$_2$Ph), 4.41 (s, 2H, CH$_2$CO$_2$H).

Example 81 alpha-Methyl 5-[[3,4-bis(phenylmethoxy)phenyl]methylene]-4-oxo-2-thioxo-3-thiazolidineacetic acid

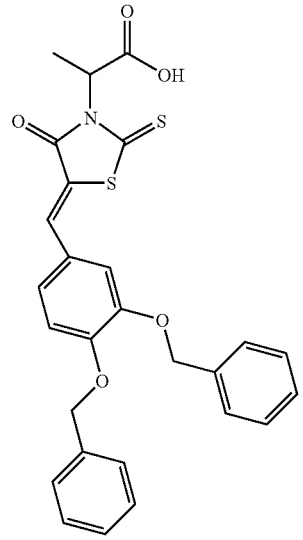

This compound was prepared from rhodanine-3-(alpha-methyl)acetic acid (213 mg, 1 eq) using the same procedure as for Example 29. The solvent was removed in vacuo and the residue dissolved in ethyl acetate (20 mL), and washed with 10% HCl (2×20 mL). The product precipitated during the work-up, so was filtered and washed with ethyl acetate. It was then suspended in water and freeze-dried overnight in vacuo to give the product as a yellow powder (321 mg, 61%) mp 178–180° C.: $^1$H NMR (CD$_3$OD) δ 7.53 (s, 1H, C=C—H), 5.51 (q, 1H, CHCH$_3$), 5.19 (s, 2H, CH$_2$Ph), 5.18 (s, 2H, CH$_2$Ph), 1.60 (d, 3H, CHCH$_3$).

Example 82

Alpha-Phenylmethyl 5-[[3,4-bis(phenylmethoxy)phenyl]methylene]-4-oxo-2-thioxo-3-thiazolidineacetic acid

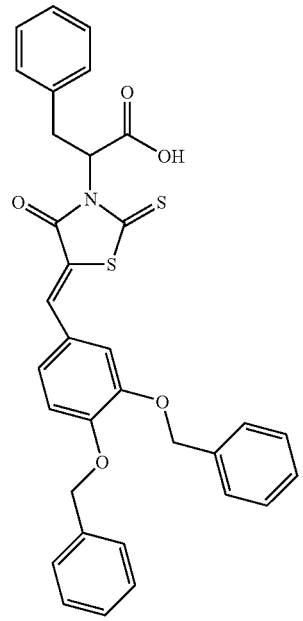

This compound was prepared from rhodanine-3-(alpha-benzyl)acetic acid (200 mg, 1 eq) using the same procedure as for Example 29. The solvent was removed in vacuo and the residue dissolved in ethyl acetate (20 mL) and washed with water (2×20 mL) and brine (20 mL). The organic solution was dried over sodium sulfate and evaporated in vacuo and the residue chromatographed on silica with petroleum ether:ethyl acetate:acetic acid (49:49:1) as eluent. The product was suspended in water and freeze-dried overnight in vacuo to give a yellow powder (189 mg, 46%) mp 76–78° C.: $^1$H NMR (d6 DMSO) δ 7.70 (s, 1H, C═C—H), 5.88 (q, 1H, CHCH$_2$), 5.25 (s, 2H, CH$_2$Ph), 5.21 (s, 2H, CH$_2$Ph), 3.49 (d, 2H, CHCH$_2$).

Example 83

5-[1-[3-Methoxy-4-(phenylmethoxy)phenyl]ethylidene]-4-oxo-2-thioxo-3-thiazolidineacetic acid

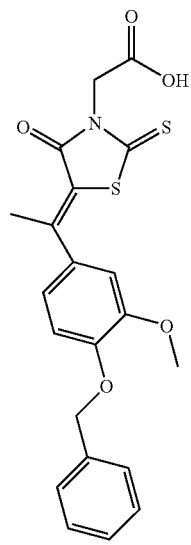

A mixture of rhodanine-3-acetic acid (291 mg, 1.52 mmol, 1 eq), 3-methoxy-4-benzyloxyacetophenone (390 mg, 1.52 mmol, 1 eq) and ammonium acetate (587 mg, 7.60 mmol, 5 eq) in toluene (5 mL) was heated to reflux and stirred for 3 days. The reaction mixture was diluted with ethyl acetate (20 mL) and washed sequentially with saturated sodium bicarbonate (20 mL), 10% HCl (2×20 mL), water (20 mL) and brine (20 mL). The organic solution was dried over sodium sulfate and evaporated in vacuo, and the residue chromatographed on silica with dichloromethane: acetic acid (49:1) as eluent. The product was recrystallized from dichloromethane and petroleum ether, suspended in water and freeze-dried overnight in vacuo to give a yellow/ orange powder (30 mg, 5%). $^1$H NMR (CDCl$_3$) δ 5.21 (s, 2H, CH$_2$Ph), 4.90 (s, 2H, CH$_2$CO$_2$H), 3.92 (s, 3H, OCH$_3$), 2.75 (s, 3H, CH$_3$).

Example 84

5-[[4-Phenylmethoxy-3-[(phenoxy)methyl]phenyl]methylene]-4-oxo-2-thioxo-3-thiazolidineacetic acid

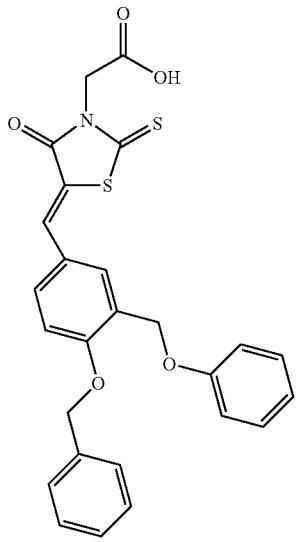

This compound was prepared from 4-phenylmethoxy-3-[(phenoxy)methyl]-benzaldehyde (90 mg, 1 eq) using the same procedure as for Example 29. A solid precipitated from the reaction mixture which was filtered and washed with acetic acid followed by diethyl ether, then dried in vacuo to give a yellow powder, 5-[[4-phenylmethoxy-3-[(phenoxy)-methyl]phenyl]methylene]-4-oxo-2-thioxo-3-thiazolidine acetic acid, (75 mg). $^1$H NMR (d6 DMSO) δ 7.77 (s, 1H, C═C—H); 5.30 (s, 2H, CH$_2$Ph); 5.18 (s, 2H, CH$_2$Ph); 4.52 (s, 2H, CH$_2$CO$_2$H).

Example 85

5-[[4-(2-Phenylethoxy)-3-(phenyloxymethyl)]phenyl]methylene]-4-oxo-2-thioxo-3-thiazolidineacetic acid

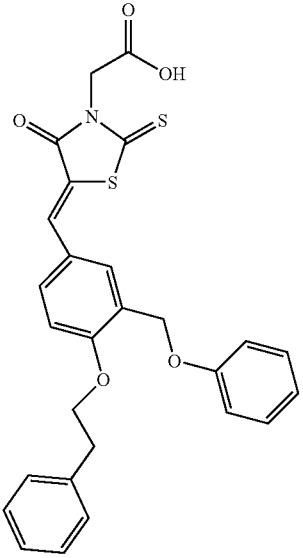

This compound was prepared from 3-(phenoxymethyl)-4-(2-phenylethoxy)benzaldehyde (105 mg, 1 eq) using the procedure described in Example 36, except that the reaction required 72 h. The product was recrystallized from diethyl ether and petroleum ether (118 mg, 74%) mp 192° C.: $^1$H NMR (d6 DMSO) δ7.84 (s, 1H, C=C—H) 7.64 (m, 1H, ArH), 7.65 (s, 1H, ArH), 6.13 (s, 1H, OCHPh), 5.03 (s, 2H, CH$_2$OPh), 4.72 (s, 2H, CH$_2$CO$_2$H), 4.35 (t, 2H, J 6.4 Hz, OCH$_2$CH$_2$Ph), 3.06 (t, 2H, J 6.4 Hz, OCH$_2$CH$_2$Ph).

Example 86

5-[[3-(Phenylmethoxy)-4-(2-phenylethoxy)phenyl]methylene]-4-oxo-2-thioxo-3-thiazolidineacetamide

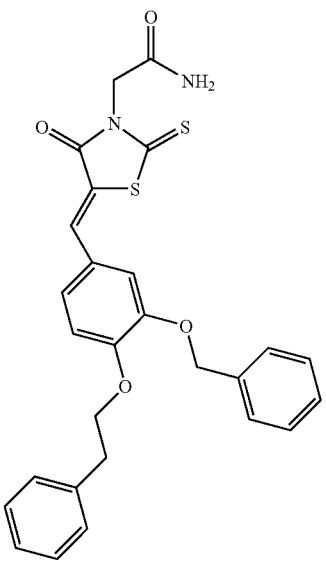

N-methylmorpholine (0.17 mL, 1.58 mmol, 4 eq) was added to a solution of 5-[[3-(phenylmethoxy)-4-(2-phenylethoxy)phenyl]methylene]-4-oxo-2-thioxo-3-thiazolidineacetic acid (200 mg, 0.40 mmol, 1 eq), 1-hydroxy-7-azabenzotriazole (108 mg, 0.79 mmol, 2 eq) and ammonium chloride (42 mg, 0.79 mmol, 2 eq) in N,N-dimethylformamide (5 mL). To this mixture was added 1-(3-dimethylaminopropyl)-3-ethylcarbodiimide hydrochloride (152 mg, 0.79 mmol, 2 eq) and the reaction mixture was stirred for 48 h. It was diluted with ethyl acetate (50 mL), and the organic solution washed with 1M HCl, (3×100 mL), then water (100 mL), dried over sodium sulfate and concentrated in vacuo. A yellow powder precipitated from the concentrate which was collected by filtration, washed with ethyl acetate and petroleum ether and dried to give the product (185 mg, 93%) mp 212–214° C.: $^1$H NMR (d6 DMSO) δ7.76 (s, 1H, C=C—H) 7.72 (broad s, 2H, exchanges with D$_2$O, NH$_2$), 5.16 (s, 2H, OCH$_2$Ph), 4.60 (s, 2H, CH$_2$CO$_2$H), 4.30 (t, 2H, J 6.4 Hz, OCH$_2$CH$_2$), 3.07 (t, 2H, J 6.4 Hz, OCH$_2$CH$_2$).

Example 87

Ethyl 5-[[3-(phenylmethoxy)-4-(2-phenethoxy)phenyl]methylene]-4-oxo-2-thioxo-3-thiazolidineacetate p-Toluenesulfonic acid (8 mg, 0.049 mmol, 0.1 eq) was added to a solution of 5-[[3-(phenylmethoxy)-4-(2-phenylethoxy)phenyl]methylene]-4-oxo-2-thioxo-3-thiazolidineacetic acid (250 mg, 0.49 mmol, 1 eq) in a mixture of anhydrous ethanol (20 mL) and triethylorthoformate (10 mL). The reaction mixture was heated at reflux for 1 week. During this time three further additions of p-toluenesulfonic acid (0.1 eq) were made to the reaction mixture. The reaction was cooled to room temperature, concentrated in vacuo and the residue purified by chromatography on silica gel. Elution with petroleum ether:ethyl acetate (9:1) gave the product as a gummy solid which was recrystallized first from ethyl acetate/petroleum ether and then from ethanol. The resultant yellow powder was washed with petroleum ether and dried to give the product (144 mg, 55%) mp 130° C.: $^1$H NMR (d6 DMSO) δ7.83 (s, 1H, C=C—H) 5.17 (s, 2H, OCH$_2$Ph), 4.82 (s, 2H, CH$_2$CO$_2$H), 4.30 (t, 2H, J 6.8 Hz, OCH$_2$CH$_2$Ph), 4.16 (q, 2H, J 7.2 Hz, CH$_2$CH$_3$), 3.07 (t, 2H, J 6.8 Hz, OCH$_2$CH$_2$Ph), 1.20 (t, 3H, J 7.2 Hz, CH$_2$CH$_3$).

Biological Assays

Example 1

PMT-1 Assay

The assay method is based upon the transfer of a radiolabelled mannose moiety from dicholphosphomannose onto a threonine hydroxyl residue in a short peptide, as catalysed by the *Candida albicans* PMT-1 enzyme. Dolicholphospho-[³H]-mannose is synthesised enzymatically from GDP-[³H]-mannose and purified by chloroform: methanol extraction.

100000 Dpm of the generated substrate is incubated with 400 μg phosphatidylcholine, 25 μg of peptide (DYATAV) and 25 μg of *Candida albicans* membrane protein in a final volume of 50 μl in 100 mM Tris/1 mM $MgCl_2$ buffer, pH 8.0. After 60 minutes at 25° C., the reaction is stopped with 50 μl of methanol. The unreacted radiolabel is removed by the addition of 150 μl of 0.4 g/ml octadecyl-functionalised silica (C18) in methanol. The C18 material is removed by centrifugation and the activity transferred to the peptide is counted in the supernatant.

Example 2

G418 Sensitivity Assay

This assay is based upon the observed increased sensitivity of the pmt1−/− *Candida* strain to Geneticin (G418) (6). 100 μl of a 0.1 $OD_{600\ nm}$ culture of *Candida albicans* (strain SC5314) is placed into a 96 well plate in the presence or absence of varying concentrations of test compound. The compounds are initially dissolved in DMSO and added to the cultures at a final DMSO concentration of 1%. G418 is added to a final concentration of 100 [2 g/ml. In the absence of PMT1 inhibition, this concentration of G418 has no effect on the proliferation of the organism. The cultures are grown overnight at 37° C. and cell density is then estimated by an $OD_{600\ nm}$ measurement. The effect of the test compound is calculated as the concentration that gives a 50% reduction in cell growth relative to the culture with G418 alone.

|  | PMT-1 Inhibition ($IC_{50}$, microM) | G418 Sensitivity ($IC_{50}$, microM) |
| --- | --- | --- |
| Example 39 | 2 | 0.65 |
| Example 42 | 1 | 0.35 |
| Example 44 | 1 | 0.6 |

The invention claimed is:
1. A compound of Formula:
5-[[3-(1-Phenylethoxy)-4-(2-phenylethoxy)]phenyl]methylene]-4-oxo-2-thioxo-3-thiazolidineacetic acid, or a salt or prodrug thereof.
2. A method for the preparation of the compound of claim 1 comprising condensation of rhodanine-3-acetic acid with a substituted benzaldehyde of Formula ArCHO under general acid-base catalysis conditions (Scheme 1):

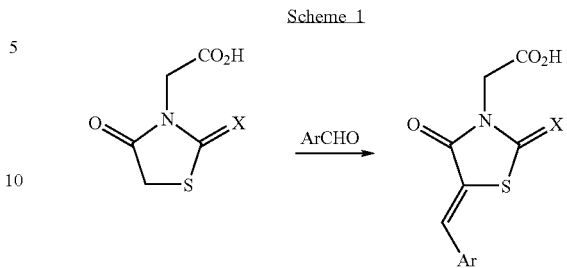

wherein X is 5, and
Ar is 3-(1-phenylethoxy)-4-(2-phenylethoxy)phenyl.
3. A pharmaceutical composition comprising the compound of claim 1 and one or more pharmaceutically acceptable carriers, excipients and or diluents.
4. A method for the treatment of a fungal infection comprising administering to an individual in need thereof, the pharmaceutical composition of claim 3.
5. The method as claimed in claim 4 wherein the fungal infection is a *Candida*, *Trichophyton*, *Microsporum*, *Cryptococcus neoformans*, *Aspergillus flavus*, *Aspergillus fumigatus*, *Coccidioides*, *Paracoccidioides*, *Histoplasma*, *Blastomyces* or *Epidermophyton* infection.
6. The method of claim 5 wherein the fungal infection is a *Candida* infection.
7. The method of claim 5 wherein the fungal infection is a *Trichophyton* infection.
8. The method of claim 5 wherein the fungal infection is a *Microsporum* infection.
9. The method of claim 5 wherein the fungal infection is a *Cryptococcus neoformans* infection.
10. The method of claim 5 wherein the fungal infection is a *Aspergillus flavus* infection.
11. The method of claim 5 wherein the fungal infection is a *Aspergillus fumigatus* infection.
12. The method of claim 5 wherein the fungal infection is a *Coccidioides* infection.
13. The method of claim 5 wherein the fungal infection is a *Paracoccidioides* infection.
14. The method of claim 5 wherein the fungal infection is a *Histoplasma* infection.
15. The method of claim 5 wherein the fungal infection is a *Blastomyces* infection.
16. The method of claim 5 wherein the fungal infection is a *Epidermophyton* infection.

* * * * *